(12) United States Patent
Caimi et al.

(10) Patent No.: US 7,897,396 B2
(45) Date of Patent: *Mar. 1, 2011

(54) ZYMOMONAS WITH IMPROVED ETHANOL PRODUCTION IN MEDIUM CONTAINING CONCENTRATED SUGARS AND ACETATE

(75) Inventors: Perry G. Caimi, Kennett Square, PA (US); Yat-Chen Chou, Lakewood, CO (US); Mary Ann Franden, Centennial, CO (US); Kyle Knoke, Newark, DE (US); Luan Tao, Havertown, PA (US); Paul V. Viitanen, West Chester, PA (US); Min Zhang, Lakewood, CO (US); Yuying Zhang, New Hope, PA (US)

(73) Assignees: E.I. du Pont de Nemours and Company, Wilmington, DE (US); Alliance for Sustainable Energy LLC

( * ) Notice: Subject to any disclaimer, the term of this patent is extended or adjusted under 35 U.S.C. 154(b) by 163 days.

This patent is subject to a terminal disclaimer.

(21) Appl. No.: 12/261,160

(22) Filed: Oct. 30, 2008

(65) Prior Publication Data
US 2009/0203099 A1    Aug. 13, 2009

Related U.S. Application Data

(60) Provisional application No. 60/983,761, filed on Oct. 30, 2007.

(51) Int. Cl.
C12N 15/74 (2006.01)
C12N 1/20 (2006.01)
C12N 15/00 (2006.01)

(52) U.S. Cl. .................. 435/471; 435/252.3; 435/440
(58) Field of Classification Search .................. None
See application file for complete search history.

(56) References Cited

U.S. PATENT DOCUMENTS

| | | | |
|---|---|---|---|
| 5,231,020 | A | 7/1993 | Jorgensen et al. |
| 5,514,583 | A | 5/1996 | Picataggio et al. |
| 5,712,133 | A | 1/1998 | Picataggio et al. |
| 5,843,760 | A | 12/1998 | Zhang et al. |
| 6,566,107 | B1 | 5/2003 | Zhang |
| 2003/0162271 | A1 | 8/2003 | Zhang et al. |
| 2007/0031918 | A1 | 2/2007 | Dunson et al. |
| 2008/0081358 | A1 | 4/2008 | Viitanen et al. |
| 2008/0187973 | A1 | 8/2008 | Viitanen et al. |

FOREIGN PATENT DOCUMENTS

| | | |
|---|---|---|
| WO | 9528476 A1 | 10/1995 |
| WO | 2004081185 A2 | 9/2004 |
| WO | 2008/051349 | 5/2008 |

OTHER PUBLICATIONS

Feldmann et al., Pentose Metabolism in *Zymomonas mobilis* Wild-Type and Recombinant Strains, Appl. Microbiol. Biotechnol., 1992, vol. 38:354-361.
Zhang et al., Metabolic Engineering of a Pentose Metabolism Pathway in Ethanologenic *Zymomonas mobilis*, Science, 1995, vol. 267:240-243.
Lawford et al.,Comparative Energetics of Glucose and Xylose Metabolism in Recombinant *Zymomonas mobilis*, Applied Biochemistry and Biotechnology, 2000, vol. 84-86:277-293.
Kim et al., Kinetic and Nuclear Magnetic Resonance Studies of Xylose Metabolism by Recombinant *Zymomonas mobilis* ZM4(pZB5), Applied and Environmental Microbiology, 2000, vol. 66:186-193.
Joachimsthal et al., Characterization of a High-Productivity Recombinant Strain of *Zymomonas mobilis* for Ethanol Production From Glucose/Xylose Mixtures, Applied Biochemistry and Biotechnology, 2000, vol. 84-86:343-356.
Kim et al., Nuclear Magnetic Resonance Studies of Acetic Acid Inhibition of Rec *Zymomonas mobilis* ZM4)pZB5), Applied Biochemistry and Biotechnology, 2000, vol. 84-86:357-370.
Joachimsthal et al., A Mutant of *Zymomonas mobilis* ZM4 Capable of Ethanol Production From Glucose in the Presence of High Acetate Concentrations, Biotechnol. Lett., 1998, vol. 20:137-142.
Jeon et al., Kinetic Analysis of Ethanol Production by an Acetate-Resistant Strain of Recombinant *Zymomonas mobilis*, Biotechnol. Letter, 2002, vol. 24:819-824.
Mohagheghi et al., Biotechnol. Lett. 2004, vol. 26:321-325.
Genbank AE008692, published May 10, 2001.
Lawford et al., The Effect of Acetic Acid on Fuel Ethanol Production by *Zymomonas*, Applied Biochemistry and Biotechnology, 1993, vol. 39-40:687-699.
Friedman, Integration Host Factor: A Protein for All Reasons, Cell, 1988, vol. 55:545-554.
Arfin et al., Global Gene Expression Profiling in *Escherichia coli* K12, J. Biol. Chem., 2000, vol. 275:29672-29684.
Arnold et al., Global Analysis of *Escherichia coli* Gene Expression During the Acetate-Induced Acid Tolerance Response, J. Bacteriol., 2001, vol. 183:2178-2186.
Genbank NP_416227, published Apr. 24, 2007.
Genbank YP_001264041, published May 8, 2007.
L. R. Lynd et al., Microbial Cellulose Utilization: Fundamentals and Biotechnology, Microbiol. Mol. Biol. Rev., 2002, vol. 66:506-577.
Agrawal, Growth Inhibition of *Zymomonas mobilis* ATCC 10988 by Ammonium Ions, Biotechnology and Bioengineering, 1989, vol. 34:278-281.
Crueger et al., Biotechnology: A Textbook of Industrial Microbiology, Second Edition,1989, Sinauer Associates, Inc., Sunderland, MA, pp. 64-74. Deshpande et al., Ethanol production from cellulose by coupled saccharification/fermentation using *Saccharomyces cerevisiae* and cellulase complex from sclerotium rolfsii UV-8 Mutant, Appl. Biochem. Biotechnol., 1992, vol. 36:227-234.
Genbank X06403, published Dec. 15, 1987.
Genbank X03043, published Dec. 18, 1985.
Seo et al., The Genome Sequence of the Ethanologenic Bacterium *Zymomonas mobilis* ZM4, Nat. Biotechnol., 2005, vol. 23:63-68.
Freundlich et al., Molecular Microbiology, vol. 6, No. 18, 1992, p. 2557-2563.
International Search Report and Written Opinion of Related PCT/US2008/081694 Mailed May 11, 2009.

*Primary Examiner* — Joanne Hama

(57) ABSTRACT

Through screening of a *Zymomonas* mutant library the himA gene was found to be involved in the inhibitory effect of acetate on *Zymomonas* performance. Xylose-utilizing *Zymomonas* strains further engineered to reduce activity of the himA gene were found to have increased ethanol production in comparison to a parental strain, when cultured in mixed-sugars medium comprising xylose, and, in particular, in the presence of acetate.

12 Claims, 14 Drawing Sheets

SEQUENCE LISTING

<160> NUMBER OF SEQ ID NOS: 26

<210> SEQ ID NO 1
<211> LENGTH: 342
<212> TYPE: DNA
<213> ORGANISM: Zymomonas mobilis

<400> SEQUENCE: 1

```
atgaataaac gctatgataa ccgcacaaac ggacagagca tgcaagctga tatcccaact     60
ttgacccgcg ccgatattac cgacatgctt taccatgaag taggtttgtc gcgggcagat    120
tccgccaaga tgatcgaaca aatgcttggt cacattacag atgccctgaa aaaaggtgaa    180
aatgtcaaaa tatctggttt tggcagcttt attctcaggg ataaaaatga acgtgttggc    240
cgtaatccta aaacagggat cgaggttcct atcgcaccaa ggcgggttct gactttccgt    300
gccagccagt tgatgcgcca gcggattatc aagggagcct aa                       342
```

<210> SEQ ID NO 2
<211> LENGTH: 27
<212> TYPE: DNA
<213> ORGANISM: artificial sequence
<220> FEATURE:
<223> OTHER INFORMATION: primer

<400> SEQUENCE: 2

```
gtgaaaggcg agatcaccaa ggtagtc                                         27
```

<210> SEQ ID NO 3
<211> LENGTH: 30
<212> TYPE: DNA
<213> ORGANISM: artificial sequence
<220> FEATURE:
<223> OTHER INFORMATION: primer

<400> SEQUENCE: 3

```
ctacctctga tagttgagtc gatacttcgg                                      30
```

<210> SEQ ID NO 4
<211> LENGTH: 38
<212> TYPE: DNA
<213> ORGANISM: artificial sequence
<220> FEATURE:
<223> OTHER INFORMATION: primer

<400> SEQUENCE: 4

```
ctactcattt cctgcaggtg gtaactcatt gcgcgctc                             38
```

<210> SEQ ID NO 5
<211> LENGTH: 38
<212> TYPE: DNA
<213> ORGANISM: artificial sequence
<220> FEATURE:
<223> OTHER INFORMATION: primer

<400> SEQUENCE: 5

```
catcttactg gcgcgccaaa aatctgcggc tgacatac                             38
```

<210> SEQ ID NO 6
<211> LENGTH: 56
<212> TYPE: DNA
<213> ORGANISM: artificial sequence
<220> FEATURE:
<223> OTHER INFORMATION: primer

```
<400> SEQUENCE: 6
actcatttcc atggcgatcg cactatgcgg ccgcaatgta gcacctgaag tcagcc         56

<210> SEQ ID NO 7
<211> LENGTH: 56
<212> TYPE: DNA
<213> ORGANISM: artificial sequence
<220> FEATURE:
<223> OTHER INFORMATION: primer

<400> SEQUENCE: 7
atctcactcc atggccggcc aactattaat taagaattga ttggctccaa ttcttg         56

<210> SEQ ID NO 8
<211> LENGTH: 39
<212> TYPE: DNA
<213> ORGANISM: artificial sequence
<220> FEATURE:
<223> OTHER INFORMATION: primer

<400> SEQUENCE: 8
cgcataactt cgtataatgt atgctatacg aagttatgc                            39

<210> SEQ ID NO 9
<211> LENGTH: 45
<212> TYPE: DNA
<213> ORGANISM: artificial sequence
<220> FEATURE:
<223> OTHER INFORMATION: synthetic oligo

<400> SEQUENCE: 9
ggccgcataa cttcgtatag catacattat acgaagttat gcgat                     45

<210> SEQ ID NO 10
<211> LENGTH: 43
<212> TYPE: DNA
<213> ORGANISM: artificial sequence
<220> FEATURE:
<223> OTHER INFORMATION: synthetic oligo

<400> SEQUENCE: 10
taaataactt cgtataatgt atgctatacg aagttatggc cgg                       43

<210> SEQ ID NO 11
<211> LENGTH: 41
<212> TYPE: DNA
<213> ORGANISM: artificial sequence
<220> FEATURE:
<223> OTHER INFORMATION: synthetic oligo

<400> SEQUENCE: 11
ccataacttc gtatagcata cattatacga agttatttaa t                         41

<210> SEQ ID NO 12
<211> LENGTH: 26
<212> TYPE: DNA
<213> ORGANISM: artificial sequence
<220> FEATURE:
<223> OTHER INFORMATION: primer

<400> SEQUENCE: 12
ataaaagcgg ccgcagcaca ggatga                                          26

<210> SEQ ID NO 13
<211> LENGTH: 26
<212> TYPE: DNA
```

```
<213> ORGANISM: artificial sequence
<220> FEATURE:
<223> OTHER INFORMATION: primer

<400> SEQUENCE: 13
ggcgttaatt aaggcaggtc agcaag                                              26

<210> SEQ ID NO 14
<211> LENGTH: 38
<212> TYPE: DNA
<213> ORGANISM: artificial sequence
<220> FEATURE:
<223> OTHER INFORMATION: primer

<400> SEQUENCE: 14
ctactcatcc tgcaggttta atgaatgagc ggatgctg                                 38

<210> SEQ ID NO 15
<211> LENGTH: 37
<212> TYPE: DNA
<213> ORGANISM: artificial sequence
<220> FEATURE:
<223> OTHER INFORMATION: primer

<400> SEQUENCE: 15
catcttactg cgatcgctga ctttccgtgc cagccag                                  37

<210> SEQ ID NO 16
<211> LENGTH: 37
<212> TYPE: DNA
<213> ORGANISM: artificial sequence
<220> FEATURE:
<223> OTHER INFORMATION: primer

<400> SEQUENCE: 16
tcactcatgg ccggccggga tatcagcttg catgctc                                  37

<210> SEQ ID NO 17
<211> LENGTH: 38
<212> TYPE: DNA
<213> ORGANISM: artificial sequence
<220> FEATURE:
<223> OTHER INFORMATION: primer

<400> SEQUENCE: 17
catcttactg gcgcgccgat atgctgcctt ccgaagtg                                 38

<210> SEQ ID NO 18
<211> LENGTH: 20
<212> TYPE: DNA
<213> ORGANISM: artificial sequence
<220> FEATURE:
<223> OTHER INFORMATION: primer

<400> SEQUENCE: 18
gttctgcgcc tgttattctg                                                     20

<210> SEQ ID NO 19
<211> LENGTH: 21
<212> TYPE: DNA
<213> ORGANISM: artificial sequence
<220> FEATURE:
<223> OTHER INFORMATION: primer

<400> SEQUENCE: 19
ctacctctga tagttgagtc g                                                   21
```

```
<210> SEQ ID NO 20
<211> LENGTH: 21
<212> TYPE: DNA
<213> ORGANISM: artificial sequence
<220> FEATURE:
<223> OTHER INFORMATION: primer

<400> SEQUENCE: 20
gatattccag tgctgatcga c                                              21

<210> SEQ ID NO 21
<211> LENGTH: 21
<212> TYPE: DNA
<213> ORGANISM: artificial sequence
<220> FEATURE:
<223> OTHER INFORMATION: primer

<400> SEQUENCE: 21
ctacgtgaaa ggcgagatca c                                              21

<210> SEQ ID NO 22
<211> LENGTH: 20
<212> TYPE: DNA
<213> ORGANISM: artificial sequence
<220> FEATURE:
<223> OTHER INFORMATION: primer

<400> SEQUENCE: 22
gatcaggtag gtgtgctcta                                                20

<210> SEQ ID NO 23
<211> LENGTH: 20
<212> TYPE: DNA
<213> ORGANISM: artificial sequence
<220> FEATURE:
<223> OTHER INFORMATION: primer

<400> SEQUENCE: 23
gcatcagaga gcatactgct                                                20

<210> SEQ ID NO 24
<211> LENGTH: 1302
<212> TYPE: DNA
<213> ORGANISM: Zymomonas mobilis

<400> SEQUENCE: 24
atgacgaaca aaatctcgtc ttcagataat ctttccaatg ctgtttcagc aacggatgac     60
aacgcttccc gtacgccaaa tctgacccgt cgcgctctcg ttggtggtgg tgttggactg    120
gccgcagctg gcgccttagc cagtggtctt caggcagcga cgcttcctgc tggtgccagc    180
caggttccga ccacgcctgc aggtcgcccg atgccttacg cgatccgccc gatgccggaa    240
gatcgtcgtt tcggttatgc tatcgtcggt ctgggtaaat atgcccttaa ccagattta    300 ccgggttttg ccggatgcca gcattcccgc atcgaagctt tggtcagcgg taacgctgaa    360
aaagctaaaa tcgttgccgc tgaatatggc gtcgatcccc gtaaaattta tgattacagc    420
aacttcgaca agatcgctaa agatccaaaa atcgacgctg tttacatcat tttgccaaac    480
tctttgcatg ctgaatttgc tatccgtgct ttcaaagccg gcaagcatgt tatgtgtgaa    540
aagccgatgg caacctctgt tgctgattgt cagcggatga tcgatgcagc caaggctgct    600
aataaaaagc tgatgatcgg ttaccgttgc cactatgatc caatgaaccg tgcagcggta    660
aaattgatcc gtgaaaacca gttgggtaaa ctgggcatgg ttaccaccga caactcagac    720
```

```
gttatggatc agaacgatcc tgcacagcag tggcgtctgc gtcgtgaact cgccggtggc    780
ggttctttga tggatatcgg tatttatggc ttgaacggta cccgttactt gctgggtgaa    840
gaaccgatcg aagtccgtgc ttacacctac agcgatccga atgatgaacg tttcgttgaa    900
gtcgaagatc gtattatttg gcagatgcgc ttcagaagcg gtgctctgtc tcatggtgca    960
tcttcttatt cgaccacgac gacttcacgt ttctcggtgc agggcgacaa agctgttctg   1020
ttgatggatc cggctaccgg atattatcag aatttgattt ctgtccagac cccaggccat   1080
gctaaccagt cgatgatgcc acagttcatc atgccagcga caaccagtt ctctgcacag    1140
ttggatcatc tggctgaagc cgtcatcaat aacaaaccag ttcgtagccc gggtgaagaa   1200
ggtatgcagg atgtgcgcct gattcaggcc atttatgaag cagctcgtac cggtcgcccc   1260
gtcaacacgg attggggtta tgtccgtcag ggtggttatt ga                      1302

<210> SEQ ID NO 25
<211> LENGTH: 1287
<212> TYPE: DNA
<213> ORGANISM: artificial sequence
<220> FEATURE:
<223> OTHER INFORMATION: GFOR coding region from  Z. mobilis with
      insertion and deletion

<400> SEQUENCE: 25
atgacgaaca aaatctcgtc ttcagataat ctttccaatg ctgtttcagc aacggatgac     60
aacgcttccc gtacgccaaa tctgacccgt cgcgctctcg ttggtggtgg tgttggactg    120
gccgcagctg cgcgccttag ccagtggtct tcaggcagcga cgcttcctgc tggtgccagc    180
caggttccga ccacgcctgc aggtcgcccg atgccttacg cgatccgccc gatgccggaa    240
gatcgtcgtt tcggttatgc tatcgtcggt ctgggtaaat atgcccttaa ccagatttta    300
ccgggttttg ccggatgcca gcattcccgc atcgaagctt tggtcagcgg taacgctgaa    360
aaagctaaaa tcgttgccgc tgaatatggc gtcgatcccc gtaaaattta tgattacagc    420
aacttcgaca agatcgctaa agatccaaaa atcgacgctg tttacatcat tttgccaaac    480
tctttgcatg ctgaatttgc tatccgtgct ttcaaagccg gcaagcatgt tatgtgtgaa    540
aagccgatgg caacctctgt tgctgattgt cagcggatga tcgatgcagc caaggctgct    600
aataaaaagc tgatgatcgg ttaccgttgc cactatgatc caatgcaccg tgcagcgatc    660
gcataacttc gtataatgta tgctatacga agttatggta ctcatggccg gcctcagaac    720
gatcctgcac agcagtggcg tctgcgtcgt gaactcgccg gtggcggttc tttgatggat    780
atcggtattt atggcttgaa cggtacccgt tacttgctgg gtgaagaacc gatcgaagtc    840
cgtgcttaca cctacagcga tccgaatgat gaacgttttcg ttgaagtcga agatcgtatt    900
atttggcaga tgcgcttcag aagcggtgct ctgtctcatg gtgcatcttc ttattcgacc    960
acgacgactt cacgtttctc ggtgcagggc gacaaagctg ttctgttgat ggatccggct   1020
accggatatt atcagaattt gatttctgtc cagaccccag gccatgctaa ccagtcgatg   1080
atgccacagt tcatcatgcc agcgacaac cagttctctg cacagttgga tcatctggct    1140
gaagccgtca tcaataacaa accagttcgt agcccgggtg aagaaggtat gcaggatgtg   1200
cgcctgattc aggccattta tgaagcagct cgtaccggtc gccccgtcaa cacggattgg   1260
ggttatgtcc gtcagggtgg ttattga                                        1287

<210> SEQ ID NO 26
<211> LENGTH: 113
<212> TYPE: PRT
<213> ORGANISM: Zymomonas mobilis
```

```
<400> SEQUENCE: 26

Met Asn Lys Arg Tyr Asp Asn Arg Thr Asn Gly Gln Ser Met Gln Ala
1               5                   10                  15

Asp Ile Pro Thr Leu Thr Arg Ala Asp Ile Thr Asp Met Leu Tyr His
            20                  25                  30

Glu Val Gly Leu Ser Arg Ala Asp Ser Ala Lys Met Ile Glu Gln Met
            35                  40                  45

Leu Gly His Ile Thr Asp Ala Leu Lys Lys Gly Glu Asn Val Lys Ile
        50                  55                  60

Ser Gly Phe Gly Ser Phe Ile Leu Arg Asp Lys Asn Glu Arg Val Gly
65                  70                  75                  80

Arg Asn Pro Lys Thr Gly Ile Glu Val Pro Ile Ala Pro Arg Arg Val
                85                  90                  95

Leu Thr Phe Arg Ala Ser Gln Leu Met Arg Gln Arg Ile Ile Lys Gly
            100                 105                 110

Ala
```

ZYMOMONAS WITH IMPROVED ETHANOL PRODUCTION IN MEDIUM CONTAINING CONCENTRATED SUGARS AND ACETATE

CROSS-REFERENCE TO RELATED APPLICATION

This application claims the benefit of U.S. Provisional Application No. 60/983,761, filed on Oct. 30, 2007, which application is incorporated herein by reference.

STATEMENT OF GOVERNMENT RIGHTS

This invention was made with United States Government support under Contract No. 04-03-CA-70224 awarded by the Department of Energy and Contract No. DE-AC36-08GO28308 between the United States Department of Energy and the Alliance for Sustainable Energy, LLC, the Manager and Operator of the National Renewable Energy Laboratory. The U.S. Government has certain rights in this invention.

FIELD OF INVENTION

The invention relates to the fields of microbiology and genetic engineering. More specifically, the himA gene, encoding the alpha subunit of the integration host factor, was found to be involved in acetate tolerance of *Zymomonas*. A strain of xylose-utilizing *Zymomonas* with a genetic modification of the himA gene was developed, which exhibits improved ethanol production in the presence of acetate.

BACKGROUND OF INVENTION

Production of ethanol by microorganisms provides an alternative energy source to fossil fuels and is therefore an important area of current research. *Zymomonas mobilis* is a bacterial ethanologen that grows on glucose, fructose, and sucrose, metabolizing these sugars to $CO_2$ and ethanol via the Entner-Douderoff pathway.

It is desirable to use hydrolyzed lignocellulosic biomass which can provide an abundantly available, low cost carbon substrate for use in fermentation for ethanol production. Xylose is the major pentose in hydrolyzed lignocellulosic materials. Though wild type strains of *Z. mobilis* cannot use xylose as a carbon source, recombinant strains that are able to grow on this sugar have been engineered (U.S. Pat. No. 5,514,583, U.S. Pat. No. 5,712,133, WO 95/28476, Feldmann et al. (1992) Appl Microbiol Biotechnol 38: 354-361, Zhang et al. (1995) Science 267:240-243). These strains are modified for expression of four enzymes needed for xylose metabolism: 1) xylose isomerase, which catalyses the conversion of xylose to xylulose; 2) xylulokinase, which phosphorylates xylulose to form xylulose 5-phosphate; 3) transketolase; and 4) transaldolase (U.S. Pat. No. 5,514,583, U.S. Pat. No. 6,566,107; Zhang et al. (1995) Science 267:240-243). Equipped with these four enzymes and the cell's normal metabolic machinery, three molecules of xylose are converted to two molecules of glucose 6-phosphate and one molecule of glyceraldehyde 3-phosphate, which are subsequently converted to ethanol and $CO_2$ on the glucose side of the pathway (FIG. 1).

Though there has been success in engineering *Z. mobilis* strains for xylose metabolism, the strains do not grow and produce ethanol as well on xylose as on glucose. Even under ideal circumstances, xylose metabolism is 3- to 4-fold slower than glucose metabolism (Lawford et al. (2000) Applied Biochemistry and Biotechnology 84-86: 277-293), and the difference becomes much greater under adverse conditions. Because of the slow carbon flux, the steady-state level of ATP is also lower with growth on xylose (Kim et al. (2000) Applied and Environmental Microbiology 66(1):186-193), and as a result *Z. mobilis* is far more susceptible to stress and inhibitors when it is grown on this sugar (Joachimsthal et al. (2000) Applied Biochemistry and Biotechnology 84-86:343-356; Kim et al. (2000) Applied Biochemistry and Biotechnology 84-6:357-370). A particular stress encountered in using hydrolyzed lignocellulosic biomass for fermentation is the presence of acetate (Kim et al. (2000) Applied Biochemistry and Biotechnology 84-86:357-370), which is released from the acetylated xylose residues in hemicellulose during pre-treatment and saccharification processes.

Mechanisms for *Z. mobilis* to cope with stress related to acetate and other organic acids remain to be elucidated, and there are no reports in the literature about the genes that play a role in this process. Using rational design to genetically engineer a strain that has higher resistance to acetate is therefore currently not an option. On the other hand, *Z. mobilis* mutants that have greater tolerance for acetate have been described (Joachimsthal et al. (1998) Biotechnol. Lett. 20(2): 137-142; Jeon et al. (2002) Biotechnol. Lett. 24:819-824; US Patent Application 20030162271). Selection after random chemical mutagenesis with nitrosoguanidine (NTG) was used to generate these mutants, but the modified genes that were responsible for the acetate-resistant phenotype were not identified in any of these cases. It was also not determined whether one mutation or multiple mutations were required for better fermentation performance in the presence of acetate. Thus it is currently not known from the studies cited above how to impart acetate tolerance to other strains of *Z. mobilis* using targeted genetic engineering.

There remains a need to identify genes involved in acetate tolerance that can be modified to produce acetate tolerant strains of *Zymomonas* for fermentation of hydrolysate, produced from pretreated and saccharified lignocellulosic biomass, to produce ethanol.

SUMMARY OF INVENTION

The present invention relates to producing ethanol using strains of xylose-utilizing *Zymomonas* that have improved performance in the presence of acetate. Applicants have discovered that acetate tolerance is affected by the himA gene encoding the alpha subunit of the integration host factor. A xylose-utilizing *Zymomonas* with a genetic modification of the himA gene has increased acetate tolerance when cultured in concentrated mixtures of glucose and xylose with acetate present. The himA modification provides reduced expression of the endogenous himA gene. Under these conditions, xylose utilization and ethanol production are significantly higher by the modified himA strain than for a comparable strain that has normal himA gene expression.

Accordingly, the invention provides a process for producing ethanol from a mixed-sugar medium comprising xylose, comprising:

(a) providing a recombinant *Zymomonas* strain capable of utilizing xylose to produce ethanol, said strain comprising at least one genetic modification which reduces expression of integration host factor alpha subunit protein (HimA); and (b) culturing the strain of (a) in a medium comprising xylose, whereby xylose is used by said strain as a carbon source for producing ethanol.

BRIEF DESCRIPTION OF THE FIGURES AND SEQUENCE DESCRIPTIONS

The invention can be more fully understood from the following detailed description, the Figures, and the accompanying sequence descriptions that form a part of this application.

FIG. 4 shows graphs of glucose utilization, xylose utilization, and ethanol production for the enriched transposon insertion mutant library culture in comparison to the control strain, ZW801-4, in medium with 100 g/L glucose, 90 g/L xylose and 6 g/L acetate (A) or with 105 g/L glucose, 100 g/L xylose, and 9 g/L acetate (B).

FIG. 5 shows graphs of growth in glucose-containing media for ZW801-4 (A) and the transposon insertion mutant, AcR#3 (B) with different amounts of potassium acetate.

FIG. 6 shows graphs of endpoint values for growth in glucose-containing media at 43 hr for ZW801-4 (A) and the transposon insertion mutant AcR#3 (B) with different acetate salts.

Figure 7:
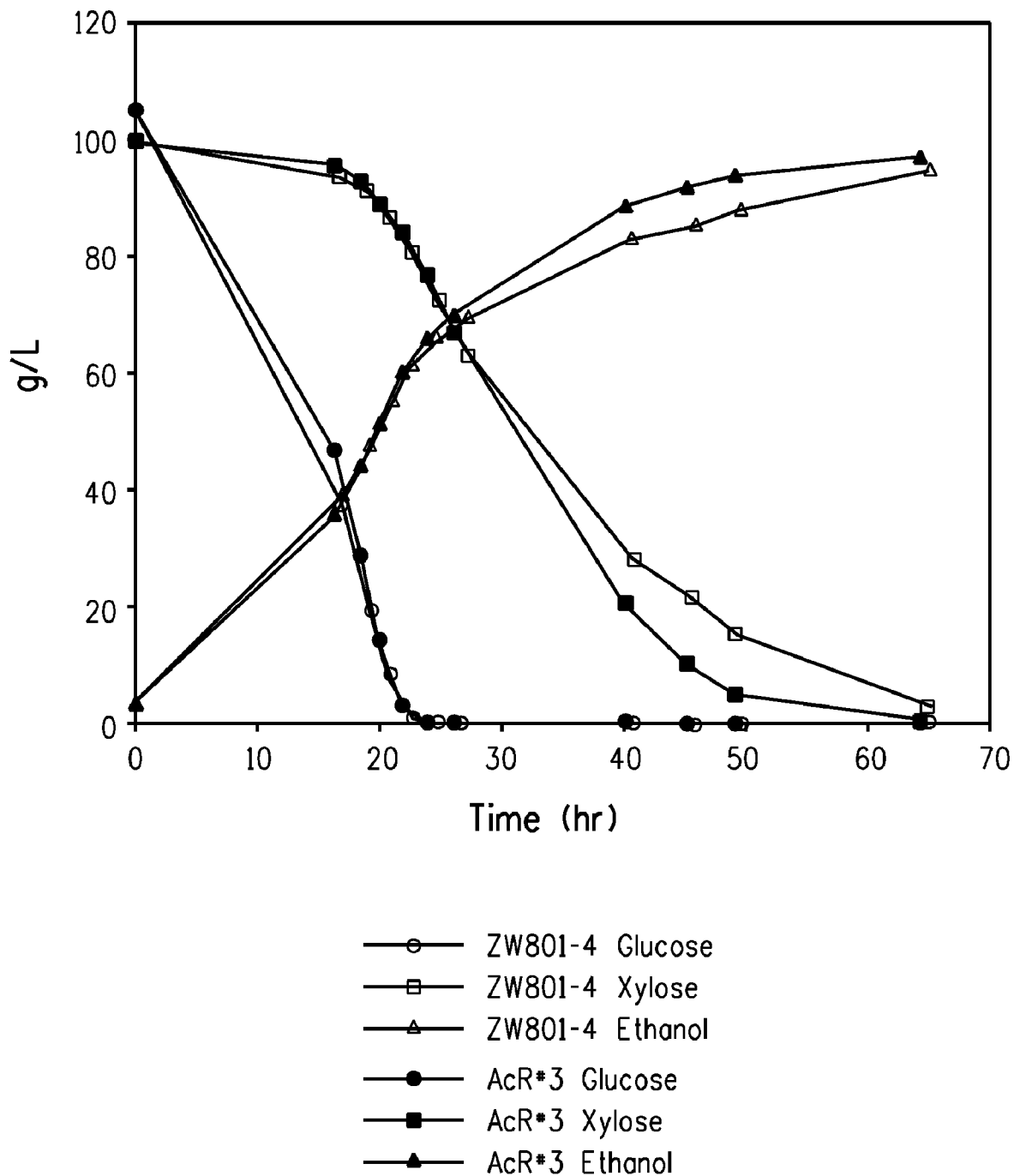

FIG. 7 shows a graph of glucose utilization, xylose utilization, and ethanol production for AcR#3 and ZW801-4 in medium with 105 g/L glucose, 100 g/L xylose, and 9 g/L acetate.

Figure 8A:
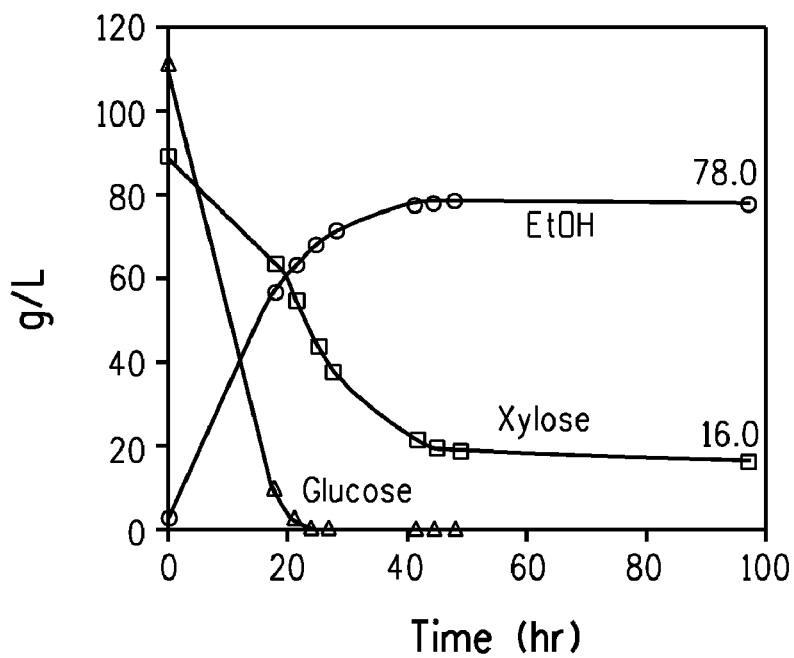
Figure 8B:
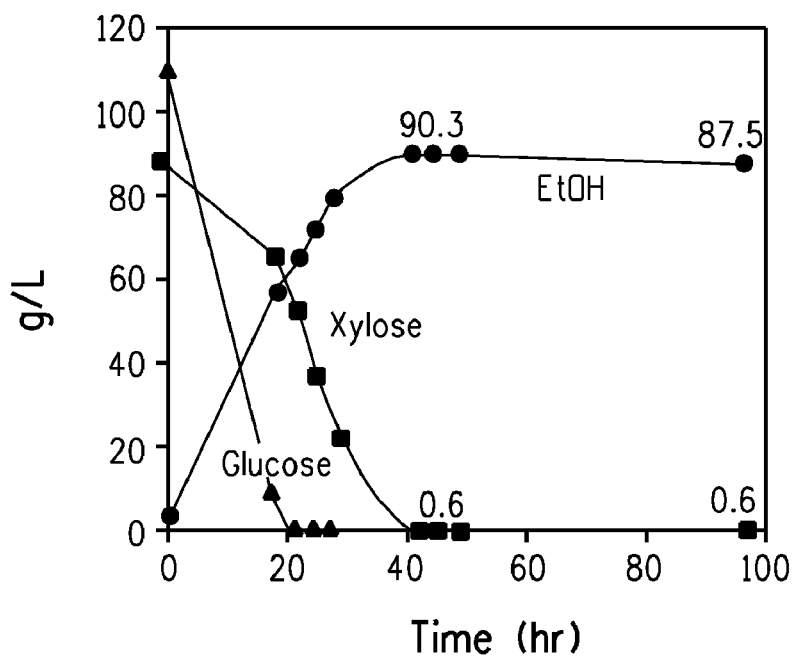

FIG. 8 shows graphs of glucose utilization, xylose utilization, and ethanol production for ZW801-4 (A) and AcR#3 (B) in 100% Mock Hydrolysate medium, which contains ~9.5 g/L of acetate and 190 mM ammonium ions, with 110 g/L glucose and 90 g/L xylose.

FIG. 9 shows maps of plasmids made during construction of a himA gene knockout vector pLDHTc139#7 (A), pLDHTc139#7-9WW (B), and pLDHSp-9WW (C).

Figure 10A:
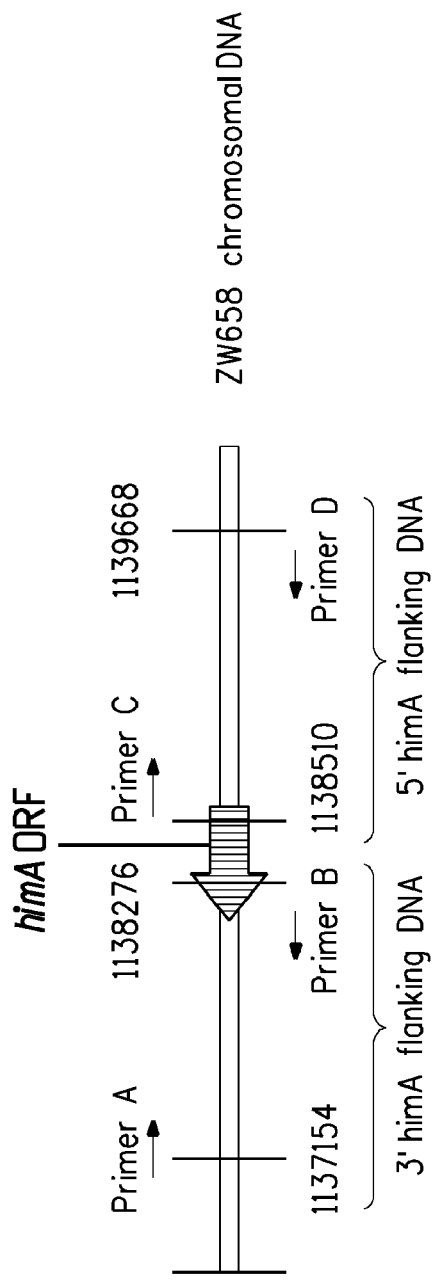
Figure 10B:
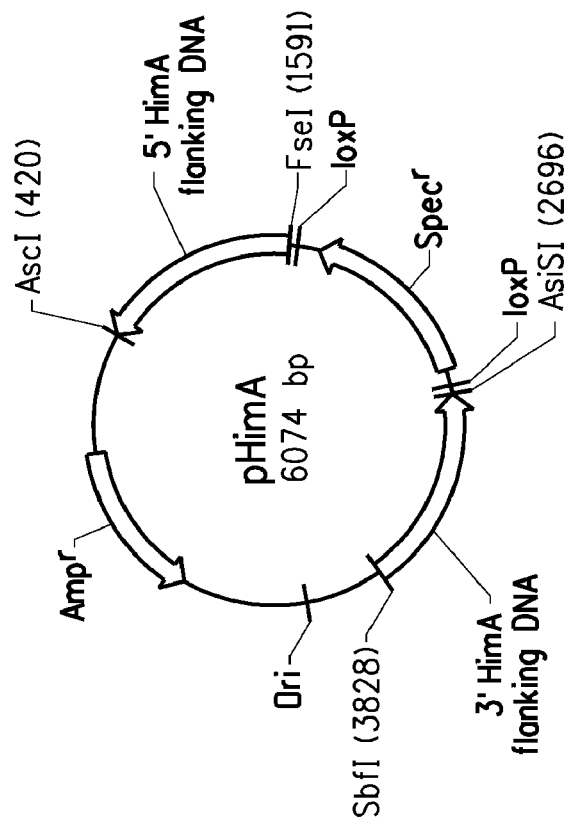

FIG. 10A shows the genomic location of primers used to prepare himA flanking DNA for insertion into the himA suicide vector, pHimA, and a circular map of the pHimA plasmid is shown in FIG. 10B.

FIG. 11 shows graphs of glucose utilization, xylose utilization, and ethanol production for ZW801-4 (A) and ZW801-4::ΔhimA (B) in 100% Mock Hydrolysate media, which contains ~9.5 g/L of acetate and 190 mM ammonium ions, with 110 g/L glucose and 90 g/L xylose.

Figure 12A:
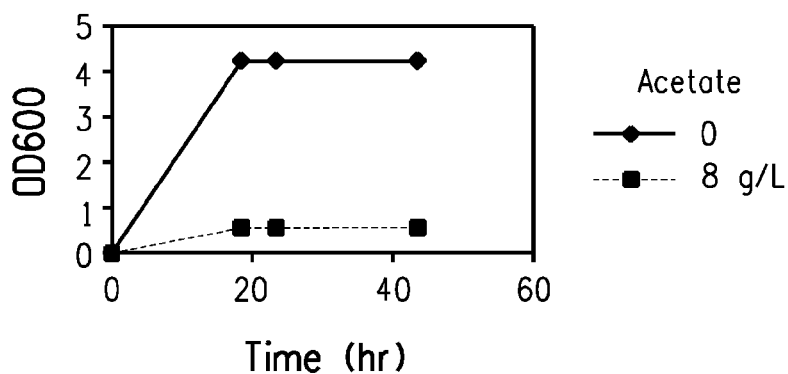
Figure 12B:
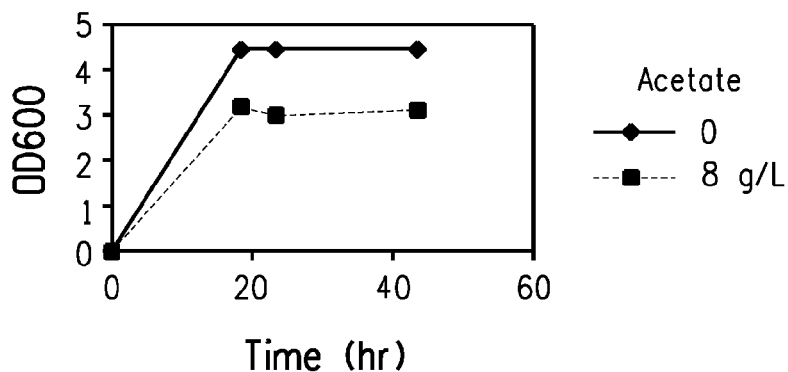
Figure 12C:
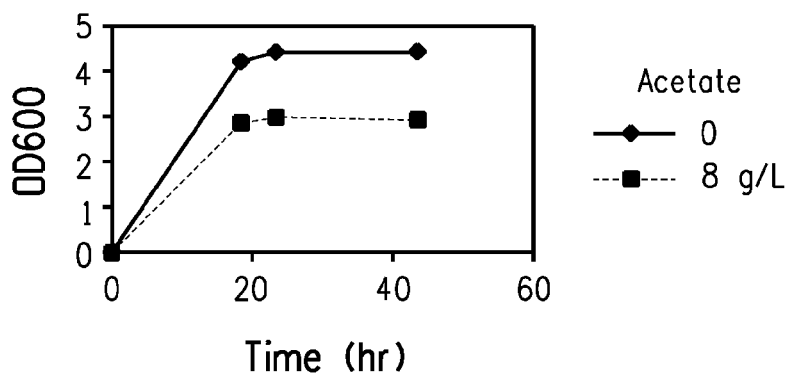

FIG. 12 shows graphs of growth in glucose-containing media for ZW801-4 (A), AcR#3 (B), and ZW801-4::ΔhimA (C) with 0 or 8 g/L of acetate added as the potassium salt.

The invention can be more fully understood from the following detailed description and the accompanying sequence descriptions which form a part of this application.

The following sequences conform with 37 C.F.R. 1.821-1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

A Sequence Listing is provided herewith on Compact Disk. The contents of the Compact Disk containing the Sequence Listing are hereby incorporated by reference in compliance with 37 CFR 1.52(e). The Compact Discs are submitted in duplicate and are identical to one another. The discs are labeled "Copy 1—Sequence Listing" and "Copy 2 Sequence listing" The discs contain the following file: CL4041 seq list.ST25.

SEQ ID NO:1 is the nucleotide sequence of the Zymomonas mobilis himA coding region.

SEQ ID NOs:2 and 3 are the nucleotide sequences of primers for sequencing transposon insertion sites.

SEQ ID NOs:4 and 5 are the nucleotide sequences of primers for PCR amplification of a DNA fragment containing the ldh gene and some surrounding DNA.

SEQ ID NOs:6 and 7 are the nucleotide sequences of primers for PCR amplification of a DNA fragment containing the tetracycline resistance cassette from pACY184.

SEQ ID NOs:8 and 9 are the nucleotide sequences of oligos used to prepare a loxP site for insertion into plasmid pLDHTc139#7.

SEQ ID NOs:10 and 11 are the nucleotide sequences of oligos used to prepare a loxP site for insertion into plasmid pLDHTc139#7-9W.

SEQ ID NOs:12 and 13 are the nucleotide sequences of primers for PCR amplification of a DNA fragment containing the spectinomycin resistance cassette from plasmid pHP15578.

SEQ ID NOs:14 and 15 are the nucleotide sequences of primers for PCR amplification of a 3' himA flanking DNA fragment.

SEQ ID NOs:16 and 17 are the nucleotide sequences of primers for PCR amplification of a 5' himA flanking DNA fragment.

SEQ ID NOs:18 and 19 are the nucleotide sequences of the PCR primers that were used to confirm that a single-crossover event had occurred between the 5' himA flanking DNA in pHimA and its chromosomal counterpart.

SEQ ID NOs:20 and 21 are the nucleotide sequences of the PCR primers that were used to confirm that a single-crossover event had occurred between the 3' himA flanking DNA in pHimA and its chromosomal counterpart.

SEQ ID NOs:22 and 23 are the nucleotide sequences of the PCR primers that were used to confirm that a double-crossover event had occurred between the 5' and 3' himA flanking DNA sequences in pHimA and the himA gene in the chromosome.

SEQ ID NO:24 is the complete nucleotide sequence of the GFOR coding region of Z. mobilis.

SEQ ID NO:25 is the complete nucleotide sequence of the disrupted GFOR coding region in ZW801-4 (from the original start codon through the original stop codon).

SEQ ID NO:26 is amino acid sequence of the Z. mobilis HimA protein.

DETAILED DESCRIPTION

The present disclosure describes processes for producing ethanol comprising culturing xylose-utilizing recombinant Zymomonas strains in medium comprising mixtures of sugars, such as glucose, xylose and acetate; wherein said strains comprise modifications to the endogenous himA gene of said strains. The modification to the himA gene reduces expression of the gene, and results in improved performance of the himA-modified Zymomonas strains when cultured in medium as described herein. Ethanol produced by the himA-modified *Zymomonas* strains may be used as an alternative energy source to fossil fuels.

The following abbreviations and definitions will be used for the interpretation of the specification and the claims.

"Integration host factor" is abbreviated IHF.

"Gene" refers to a nucleic acid fragment that expresses a specific protein, which may include regulatory sequences preceding (5' non-coding sequences) and following (3' non-coding sequences) the coding sequence. "Native gene" or "wild type gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes.

The term "genetic construct" refers to a nucleic acid fragment that encodes for expression of one or more specific proteins. In the gene construct the gene may be native, chimeric, or foreign in nature. Typically a genetic construct will comprise a "coding sequence". A "coding sequence" refers to a DNA sequence that codes for a specific amino acid sequence.

"Promoter" or "Initiation control regions" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters".

The term "expression", as used herein, refers to the transcription and stable accumulation of sense (mRNA) or antisense RNA derived from a gene. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

The term "messenger RNA (mRNA)" as used herein, refers to the RNA that is without introns and that can be translated into protein by the cell.

The term "non-functional gene" as used herein refers to a gene that does not express the encoded protein normally as in the wild type strain where the gene is endogenous. Expression of a non-functional gene may be disrupted at any level, such as transcription, RNA processing, or translation. A non-functional gene typically has little or no expression of the encoded protein. However it may also code for a modified protein that has lower enzyme activity than the wild type protein.

The term "transformation" as used herein, refers to the transfer of a nucleic acid fragment into a host organism, resulting in genetically stable inheritance. The transferred nucleic acid may be in the form of a plasmid maintained in the host cell, or some transferred nucleic acid may be integrated into the genome of the host cell. Host organisms containing the transformed nucleic acid fragments are referred to as "transgenic" or "recombinant" or "transformed" organisms.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "selectable marker" means an identifying factor, usually an antibiotic or chemical resistance gene, that is able to be selected for based upon the marker gene's effect, i.e., resistance to an antibiotic, wherein the effect is used to track the inheritance of a nucleic acid of interest and/or to identify a cell or organism that has inherited the nucleic acid of interest.

The term "high concentration of mixed sugars" refers to a total sugar concentration in the medium that results in inhibition of growth of xylose-utilizing *Zymomonas*. This typically occurs when the total sugar concentration exceeds about 100 g/L, and the severity of the effect is greater at higher sugar concentrations. However, the exact sugar concentration where growth inhibition starts to occur is highly dependent on other components in the medium.

The term "fermentable sugar" refers to oligosaccharides and monosaccharides that can be used as a carbon source by a microorganism in a fermentation process.

The term "lignocellulosic" refers to a composition comprising both lignin and cellulose. Lignocellulosic material may also comprise hemicellulose.

The term "cellulosic" refers to a composition comprising cellulose and additional components, including hemicellulose.

The term "saccharification" refers to the production of fermentable sugars from polysaccharides.

The term "pretreated biomass" means biomass that has been subjected to pretreatment prior to saccharification.

"Biomass" refers to any cellulosic or lignocellulosic material and includes materials comprising cellulose, and optionally further comprising hemicellulose, lignin, starch, polysaccharides, oligosaccharides and/or monosaccharides. Biomass may also comprise additional components, such as protein and/or lipid. Biomass may be derived from a single source, or biomass can comprise a mixture derived from more than one source; for example, biomass could comprise a mixture of corn cobs and corn stover or fiber, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers and animal manure.

"Biomass hydrolysate" refers to the product resulting from saccharification of biomass. The biomass may also be pretreated prior to saccharification.

Standard recombinant DNA and molecular cloning techniques used here are well known in the art and are described by Sambrook, J., Fritsch, E. F. and Maniatis, T. *Molecular Cloning: A Laboratory Manual*, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. *Experiments with Gene Fusions*; Cold Spring Harbor Laboratory: Cold Spring Harbor, N.Y., 1984; and by Ausubel, F. M. et al., In *Current Protocols in Molecular Biology*, published by Greene Publishing and Wiley-Interscience, 1987.

The present invention relates to engineered strains of xylose-utilizing *Zymomonas* that have improved performance in the presence of acetate. Acetate is an inhibitor of *Zymomonas* which when present during fermentation, reduces growth and ethanol production. Acetate is a metabolic by-product in *Zymomonas* and is also a component of pretreated and saccharified biomass. Therefore a challenge in using sugars derived from biomass for fermentation is to overcome inhibitory effects of acetate on the biocatalyst for improved ethanol production. It is shown herein that engineering a disruption of the endogenous himA gene in xylose-utilizing *Z. mobilis* improves fermentation performance, including xylose utilization and ethanol production, when the fermentation medium comprises acetate. Further, the present invention relates to a process for producing ethanol wherein the present *Zymomonas* strains are cultured in medium comprising xylose.

Xylose-Utilizing *Zymomonas* Host Strain

Figure 1:
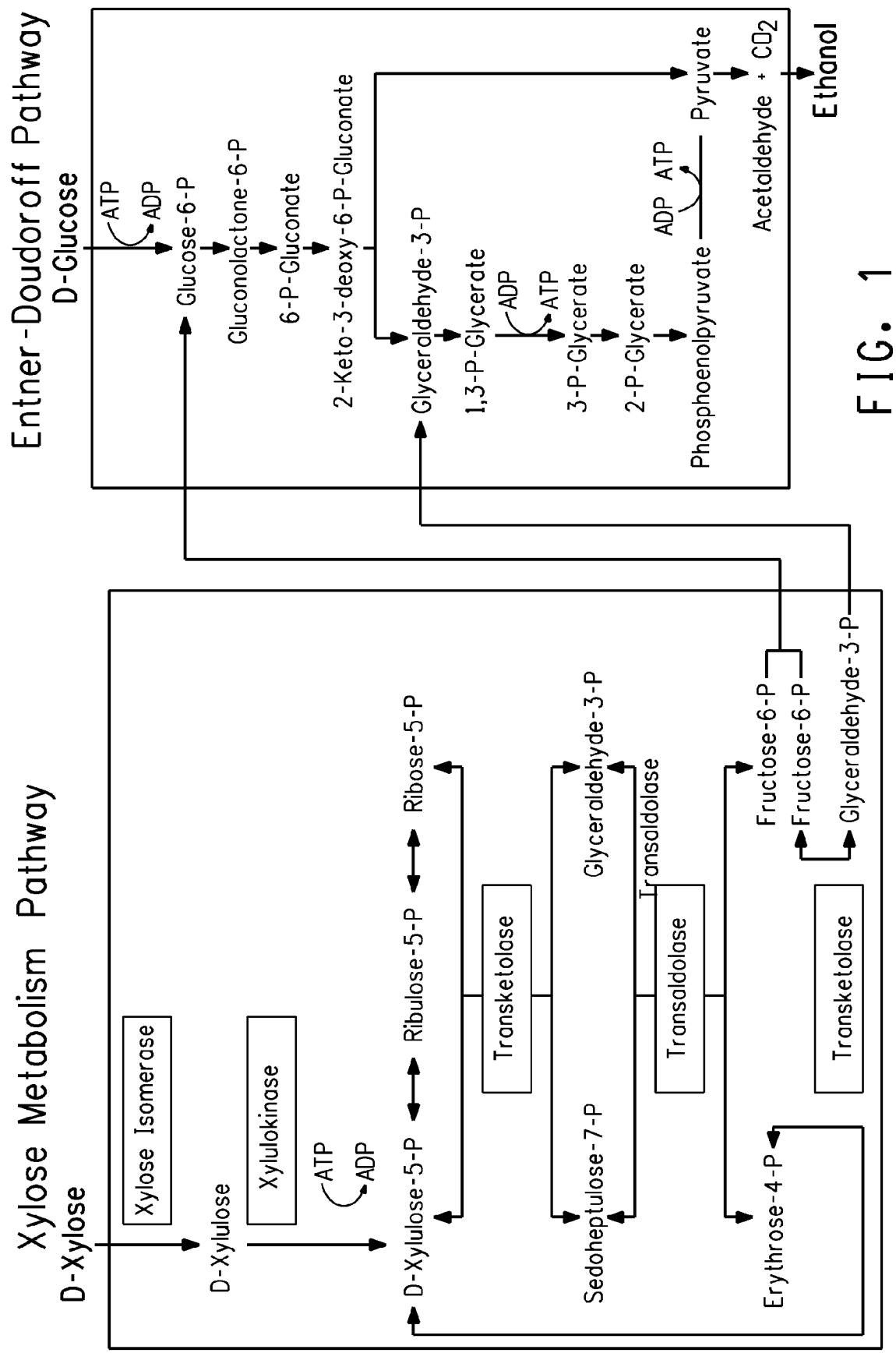
FIG. 1 shows a diagram of the four enzymes (boxed) that have been used to engineer Z. mobilis for xylose utilization and biochemical pathways for ethanol production using xylose.

Any strain of *Zymomonas*, including a *Z. mobilis* strain, that is able to utilize xylose as a carbon source may be used as a host for preparing strains used in the present invention. Strains of *Zymomonas* that have been engineered for xylose fermentation to ethanol are particularly useful. Endogenous genes may provide part of the metabolic pathway, or may be altered by any known genetic manipulation technique to provide a protein with enzyme activity useful for xylose metabolism. For example, the endogenous transketolase may complement other introduced enzyme activities in creating a xylose utilization pathway. Typically four genes have been introduced into *Z. mobilis* for expression of four enzymes involved in xylose metabolism (FIG. 1) as described in U.S. Pat. No. 5,514,583, which is herein incorporated by reference. These include genes encoding xylose isomerase, which catalyzes the conversion of xylose to xylulose and xylulokinase, which phosphorylates xylulose to form xylulose 5-phosphate. In addition, transketolase and transaldolase, two enzymes of the pentose phosphate pathway, convert xylulose 5-phosphate to intermediates (fructose 6-phosphate and glyceraldehydes 3-phosphate) that couple pentose metabolism to the glycolytic Entner-Douderoff pathway permitting the metabolism of xylose to ethanol. DNA sequences encoding these enzymes may be obtained from any of numerous microorganisms that are able to metabolize xylose, such as enteric bacteria, and some yeasts and fungi. Sources for the coding regions include *Xanthomonas*, *Klebsiella*, *Escherichia*, *Rhodobacter*, *Flavobacterium*, *Acetobacter*, *Gluconobacter*, *Rhizobium*, *Agrobacterium*, *Salmonella*, *Pseudomonads*, and *Zymomonas*. Particularly useful are the coding regions of *E. coli*.

The encoding DNA sequences are operably linked to promoters that are expressed in *Zymomonas* cells such as the promoter of *Zymomonas* glyceraldehyde-3-phosphate dehydrogenase (GAP promoter), and *Zymomonas* enolase (ENO promoter). The coding regions may individually be expressed from promoters, or two or more coding regions may be joined in an operon with expression from the same promoter. The resulting chimeric genes may be introduced into *Zymomonas* and maintained on a plasmid, or integrated into the genome using, for example, homologous recombination, site-directed integration, or random integration. Xylose-utilizing strains that are of particular use include CP4(pZB5) (U.S. Pat. No. 5,514,583), ATCC31821/pZB5 (U.S. Pat. No. 6,566,107), 8b (US 20030162271; Mohagheghi et al., (2004) Biotechnol. Lett. 25; 321-325), and ZW658 (ATTCC #PTA-7858).

*Zymomonas* strains that are additionally engineered to utilize sugars other than xylose, which they do not normally use, may also be used in the present process. An example is a xylose-utilizing strain of *Z. mobilis* that was further engineered for arabinose utilization is described in U.S. Pat. No. 5,843,760, which is herein incorporated by reference.

*Zymomonas* strains that are additionally engineered for reduced production of the unwanted by-product xylitol may also be used. These strains are described in commonly owned and co-pending U.S. patent application Ser. No. 11/862,566 and pending US patent publication #US20080187973 A1, which are herein incorporated by reference. The described strains ZW800, ZW801-4, and ZW801-6 have a disrupted gene encoding glucose-fructose oxidoreductase (GFOR). Disruption of expression of the GFOR gene may be accomplished using the same methods described below for disrupting the himA gene, using the known sequence of the GFOR coding region (SEQ ID NO:24). DNA sequences surrounding the GFOR coding sequence are also useful in some modification procedures and are available for *Zymomonas* in the complete genome sequence (GenBank Accession #AE008692). Reduced expression of GFOR was found to reduce xylitol production and enhance ethanol production.

Discovery of himA Involvement in Acetate Tolerance

Although the mechanistic basis for the inhibitory effects of acetate on growth and productivity of *Zymomonas* is reasonably well understood (Lawford et al. (1993) Applied Biochemistry and Biotechnology 39-40: 687-699; Kim et al. (2000) Applied Biochemistry and Biotechnology 84-86:357-370), genes that play a role in acetate tolerance have not been identified for this microorganism. Applicants have surprisingly found that genetic manipulation of the himA gene allows *Zymomonas* to perform better in the presence of inhibitory concentrations of acetate. Specifically, applicants have found that disrupting the *Zymomonas* himA gene improves growth and ethanol production in acetate-containing media. The mutant library enrichment process that was used to discover the role of himA in acetate-resistance described herein in Examples 1 and 2 is a completely unbiased approach and was not based on any predicted result.

The finding that disruption of the *Zymomonas* himA gene improves performance in the presence of acetate is unexpected, as there are no indications or suggestions in the literature that this gene plays a role in acetate tolerance for *Zymomonas* or any other microorganism. The protein encoded by the himA gene, referred to herein as "HimA"

protein, is the alpha subunit (SEQ ID NO:26) of the integration host factor (IHF), a protein which also includes a beta subunit encoded by the himD gene. Thus, IHF is a heterodimeric protein that is comprised of two closely related subunits. IHF has been studied in *E. coli* and shown to be a DNA binding and DNA bending protein that is involved in DNA recombination, DNA replication, and regulation of gene expression (Friedman (1988) Cell 55:545-554; Arfin et al. (2000) J. Biol. Chem. 275: 29672-29684). Gene expression profiling experiments in *E. coli* have shown that himA gene inactivation significantly alters the expression level of at least 120 genes, and that this manipulation activates more genes than it represses (Arfin et al. (2000) J. Biol. Chem. 275: 29672-29684). It is also known that the *E. coli* himA gene is most actively transcribed when cells transition from exponential phase to the stationary phase, and the himA gene product is thought to play a role in this process. Thus himA affects a broad range of DNA processes and is a regulator of gene expression in *E. coli*, but none of the many genes that it is thought to regulate are clearly related to acetate tolerance. Furthermore, global analysis of gene expression in *E. coli* after exposure to an inhibitory concentration of acetate has been examined using microarrays, and of the 86 genes that were effected by this treatment the himA gene was not among them (Arnold et al. (2001) J. Bacteriol. 183: 2178-2186). Finally, nothing is known about the role of the himA gene in *Zymomonas*. Nor are we aware of any reports in the literature that show that himA gene inactivation results in any type of beneficial effect. Indeed, it is surprising that this would be the case considering the large number of genes and proteins that are probably effected by this manipulation. It is therefore reasonable to conclude that those skilled in the art could not have predicted that inactivation of the himA gene would confer greater tolerance to acetate for *Z. mobilis* or any other microorganism.

The *Zymomonas*HimA protein is 46% identical to the *E. Coli* homolog (GenBank accession number NP_416227). The most closely related known protein is the HimA homolog of *Sphingomonas wittichii* (GenBank accession number YP_001264041) which is 67% identical, as determined by a tBLASTx search against the NCBI database using the *Z. mobilis* himA coding region (SEQ ID NO:1) as the query sequence.

Altering himA Gene Expression

A xylose-utilizing *Z. mobilis* strain of the present invention is genetically modified such that there is reduced or no expression of integration host factor alpha subunit protein (HimA). Typically, reduction in HimA protein expression is accomplished through a modification that reduces expression of the himA gene. Reducing HimA protein expression may include modifications that for example reduce translation of the encoding mRNA, or reduce stability of the HimA protein. Reduced expression of the HimA protein results in improved performance in the presence of acetate. Any genetic modification method known by one skilled in the art for reducing the expression of a protein may be used to alter HimA expression. Methods include, but are not limited to, deletion of the entire or a portion of the himA gene, inserting a DNA fragment into the himA gene (in either the promoter or coding region) so that the encoded protein cannot be expressed, introducing a mutation into the himA coding region which adds a stop codon or frame shift such that a functional protein is not expressed, and introducing one or more mutations into the himA coding region to alter amino acids so that a non-functional or a less functionally active protein is expressed. In addition, himA expression may be blocked by expression of an antisense RNA or an interfering RNA, and constructs may be introduced that result in cosuppression. All of these methods may be readily practiced by one skilled in the art making use of the known himA coding sequence (SEQ ID NO:1), as well as the *Z. mobilis* DNA sequence that surrounds the himA coding sequence, that is available in the complete *Z. mobilis* genome sequence (GenBank Accession #AE008692).

A particularly suitable method for creating a genetically modified himA strain, as exemplified herein in Examples 5 and 6, is using homologous recombination mediated by himA flanking DNA sequences bounding a spectinomycin resistance or other marker gene, leading to insertion of the marker gene in the himA coding region such that a functional protein is not expressed. In addition, the marker gene may be bounded by site-specific recombination sites, so that following expression of the corresponding site-specific recombinase, the resistance gene is excised from the himA gene. The site-specific recombination leaves behind a recombination site which disrupts expression of the himA gene. The homologous recombination vector may be constructed to also leave a deletion in the himA gene following excision of the marker, as is well known to one skilled in the art.

It is preferred to completely eliminate the expression of himA, however greatly reduced expression of himA is also an embodiment of the present invention. In this case, a non-functional himA gene refers to not functioning in the normal manner such that lower than normal levels of encoded protein are present. Some methods of gene inactivation may result in some remaining low-level expression, such as co-suppression. Herein, a modified himA strain refers to a genetically modified strain with reduced or no HimA enzyme activity.

Performance of himA Modified Strain

A himA modified xylose-utilizing *Z. mobilis* strain of the present invention has improved performance when cultured in a xylose containing medium that also contains acetate. It is desirable to use sugars that are produced from biomass saccharification in culture medium for xylose-utilizing *Z. mobilis*. Typically biomass is pretreated, for example as described in Patent Publication WO2004/081185 and in commonly owned and co-pending US publication US20070031918A1, and then treated with saccharification enzymes as reviewed in Lynd, L. R., et al. (Microbiol. Mol. Biol. Rev. (2002) 66:506-577). The hydrolysate product of biomass pretreatment and saccharification which contains xylose and other sugars also typically contains acetate. Hemicellulose in biomass contains acetylated xylose residues and the acetate is released under very mild conditions. Although removing the acetate from processed biomass is one way to resolve the problem, incorporating this step would substantially increase the cost of manufacturing cellulosic ethanol. Consequently, being able to engineer *Z. mobilis* strains to provide higher tolerance for acetate is a substantial improvement.

The improved performance in the presence of acetate as assayed herein includes growth, utilization of xylose, and production of ethanol. Improved performance of a himA modified xylose-utilizing *Z. mobilis* strain is relative to a strain with the same genetic features (an isogenic strain), but lacking a modification of the himA gene. The parental strain used for genetic modification of the himA gene is typically used in this comparison. Improvement may be seen at any level of acetate in which an unmodified himA strain does not reach its full potential for growth and ethanol production. Depending on the composition of the medium and pH control, improvement typically occurs when the concentration of acetate is about 5 g/L or higher. The extent of "acetate inhibition" also depends on the pH since the inhibitory species is actually acetic acid, and the equilibrium of acetic acid and acetate is dependent upon pH. Without control of pH, Z.

*mobilis* rapidly acidifies the culture medium, like other gram-negative bacteria. With a drop in pH from 5.8 to 4.8, the concentration of acetic acid increases by 5-fold due to the ~4.8 p$K_A$ of acetic acid. Thus the actual concentration of acetic acid (the inhibitor) depends on the pH of the culture medium as well as the total amount of the protonated and unprotonated species that is present in the culture medium.

In a concentrated mixture of glucose and xylose with acetate present, the unmodified and modified himA strains utilize glucose similarly under pH controlled conditions, with the glucose largely being consumed prior to xylose consumption. However, during the late stage of fermentation after all the glucose has been depleted the himA modified strain is able to convert more xylose to ethanol than the isogenic parent strain that has normal himA gene expression.

The level of increased ethanol production conferred by the himA gene modification is dependent upon the components of the culture medium in pH controlled conditions, including the levels and ratios of types of sugars and presence of other inhibitors. For example, in the presence of 126 g/L glucose, 107 g/L xylose and 10% acetate there was a 4% increase in the ethanol titer for the himA modified strain as compared to the isogenic strain with no himA modification. When the culture medium also contains other inhibitors, the increased ethanol production can be even greater. For example, in a mock hydrolysate medium that includes 110 g/L glucose, 90 g/L xylose, ~9.5 g/L acetate and 190 mM ammonium ions (another inhibitor of *Z. mobilis* growth (Agrawal (1989) Biotechnology and Bioengineering 34: 278-281) that may be present in biomass hydrolysate at this concentration), there was about an 11% increase in ethanol production and a more complete utilization of xylose. Thus, under more severe conditions, the differential in ethanol production between a modified himA strain and an isogenic unmodified himA strain might even be greater than the examples cited. For example, at higher sugar concentrations or when other hydrolysate-derived inhibitors are also present in addition to ammonium ions and acetate. Therefore depending on the culture conditions, the improvement in ethanol production may be at least about 4% or higher.

Fermentation for Ethanol Production

In the process of the present invention, the present himA modified, xylose-utilizing strain is cultured in "mixed-sugars medium" that is any medium that contains any mixture of sugars that includes at least some xylose. In particular, the present strain may be cultured in biomass hydrolysate, or a dilution of biomass hydrolysate ath comprises some xylose. Biomass saccharification produces sugars in a biomass hydrolysate that may typically include a mixture of xylose with glucose, fructose, sucrose, galactose, mannose, and/or arabinose. Preferred is a mixed sugars composition that includes xylose and glucose, where additional sugars may be present. The ratio of different sugars may vary in the mixture, with xylose typically at least about 10% of the total amount of sugars. Preferably xylose is between about 40% and about 60%. Fructose is present in sugars produced by saccharification of some biomass such as sugar cane bagasse, and may replace a portion of xylose or glucose, such that xylose remains at least about 10% of the sugar mixture. In addition, arabinose is derived from hemicellulose and thus is a typical component of mixed sugars derived from saccharified biomass containing hemicellulose. During fermentation with the present strains, xylose is one of the sugars that is used as a carbon source for production of ethanol. For maximal ethanol production and efficiency of fermentation it is desirable to culture the present himA modified, xylose-utilizing strain in medium containing a concentrated mixture of sugars, including xylose. This allows the direct use of biomass saccharification sugars, or use with little dilution, thereby reducing fermentation volumes, which is desirable for commercial scale ethanol production. High sugars concentrations are used so that greater concentrations of ethanol may be produced. The mixed sugars concentration in the fermentation medium is typically at least about 120 g/L and up to about 300 g/L. Particularly useful is a high concentration of mixed sugars that is between about 150 g/L and about 235 g/L.

In the high concentration mixed sugars conditions desired for production of ethanol, sorbitol may be included in the fermentation medium used to culture the himA modified, xylose-utilizing *Z. mobilis* as described in commonly owned and co-pending US publication #US20080081358A1, which is herein incorporated by reference. Sorbitol (D-Sorbitol and/or L-Sorbitol) may be present in the medium at concentrations that are between about 2 mM and 200 mM. More suitable final concentrations in the medium are concentrations between about 2 mM and 100 mM, with concentrations between 5 mM and 20 mM preferred. Mannitol may be used in the medium instead of sorbitol, or in combination with sorbitol. In addition, it was found that galactitol and/or ribitol may be used in place of or in combination with sorbitol or mannitol. Sorbitol, mannitol, galactitol, ribitol or combinations thereof are all used in the same concentrations as described for sorbitol.

*Z. mobilis* is cultured in the medium where fermentation occurs and ethanol is produced. The fermentation is run without supplemented air, oxygen, or other gases (which may include conditions such as anaerobic, microaerobic, or microaerophilic fermentation), for at least about 24 hours, and may be run for 48 hours or more. The timing to reach maximal ethanol production is variable, depending on the fermentation conditions. Typically, if inhibitors are present in the medium, a longer fermentation period is required. The fermentations may be run at temperatures that are in a range between about 25° C. and about 40° C., and at a pH of about 4.5 to about 7.5. Particularly suitable are temperatures between about 30° C. and about 37° C. It is also particularly suitable to maintain the pH at least about 1 pH unit above the p$K_A$ of acetic acid, bringing the pH to between about 5.8 and 7.5, to decrease the ratio of acetic acid to acetate.

The himA modified xylose-utilizing *Z. mobilis* may be cultured in medium containing mixed sugars including xylose in laboratory scale fermenters, and in scaled up fermentation where commercial quantities of ethanol are produced. In addition, the medium may contain acetate as described above. Where commercial production of ethanol is desired, a variety of culture methodologies may be applied. For example, large-scale production from himA modified xylose-utilizing *Z. mobilis* may be produced by both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells typically moderate through a static lag phase to a growth phase and finally to a stationary phase where growth rate is diminished or halted. If untreated, cells in the stationary phase will eventually die.

Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable for culture of himA modified xylose-utilizing *Z. mobilis* and comprise a typical batch system with the exception that the substrate is added in increments as the culture progresses. Fed-Batch systems are useful when catabolite repression is apt to inhibit the metabolism of the cells and where it is desirable to have limited amounts of substrate in the medium. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of ethanol may also be accomplished with a continuous culture. Continuous cultures are open systems where a defined culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

Continuous or semi-continuous culture allows for the modulation of one factor or any number of factors that affect cell growth, metabolism, or end product concentration. For example, one method will maintain a limiting nutrient such as the carbon source or nitrogen level at a fixed rate and allow all other parameters to moderate. In other systems a number of factors affecting growth or metabolism can be altered continuously while the cell concentration, measured by medium turbidity, is kept constant. Continuous systems strive to maintain steady state growth conditions and thus the cell loss due to medium being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Particularly suitable for ethanol production is a fermentation regime as follows. The desired himA modified xylose-utilizing *Z. mobilis* strain is grown in shake flasks in semi-complex medium at about 30° C. to about 37° C. with shaking at about 150 rpm in orbital shakers and then transferred to a 10 L seed fermentor containing similar medium. The seed culture is grown in the seed fermentor anaerobically until $OD_{600}$ is between 3 and 6, when it is transferred to the production fermentor where the fermentation parameters are optimized for ethanol production. Typical inoculum volumes transferred from the seed tank to the production tank range from about 2% to about 20% v/v. Typical fermentation medium contains minimal medium components such as potassium phosphate (1.0-10.0 g/l), ammonium sulfate (0-2.0 g/l), magnesium sulfate (0-5.0 g/l), a complex nitrogen source such as yeast extract or soy based products (0-10 g/l). A final concentration of about 5 mM sorbitol or mannitol is present in the medium. Mixed sugars including xylose and at least one additional sugar such as glucose (or sucrose), providing a carbon source, are continually added to the fermentation vessel on depletion of the initial batched carbon source (50-200 g/l) to maximize ethanol rate and titer. Carbon source feed rates are adjusted dynamically to ensure that the culture is not accumulating glucose in excess, which could lead to build up of toxic byproducts such as acetic acid. In order to maximize yield of ethanol produced from substrate utilized, biomass growth is restricted by the amount of phosphate that is either batched initially or that is fed during the course of the fermentation. The pH of the fermentation broth is controlled/maintain by automated base addition using ammonium hydroxide, potassium hydroxide, sodium hydroxide, or other strong bases. The temperature of the fermentor is controlled in the desired range. In order to minimize foaming, antifoam agents (any class-silicone based, organic based etc) are added to the vessel as needed. An antibiotic, for which there is an antibiotic resistant marker in the strain, such as kanamycin, may be used optionally to minimize contamination.

Any set of conditions described above, and additionally variations in these conditions that are well known to one skilled in the art, are suitable conditions for production of ethanol by the present xylose-utilizing, himA modified recombinant *Zymomonas* strains.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used here are well known in the art and are described by Sambrook, J., Fritsch, E. F. and Maniatis, T., *Molecular Cloning: A Laboratory Manual*, $2^{nd}$ ed., Cold Spring Harbor Laboratory: Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory: Cold Spring Harbor, N.Y. (1984); and by Ausubel, F. M. et al., *Current Protocols in Molecular Biology*, published by Greene Publishing Assoc. and Wiley-Interscience, Hoboken, N.J. (1987).

The meaning of abbreviations is as follows: "kb" means kilobase(s), "bp" means base pairs, "nt" means nucleotide(s), "hr" means hour(s), "min" means minute(s), "seq" means second(s), "d" means day(s), "L" means liter(s), "ml" means milliliter(s), "µL" means microliter(s), "µg" means microgram(s), "ng" means nanogram(s), "g" means grams, "mM" means millimolar, "µM" means micromolar, "nm" means nanometer(s), "µmol" means micromole(s), "pmol" means picomole(s), "Cm" means chloramphenicol, "Cm'" means chloramphenicol resistant, "Spec'" means spectinomycin resistance, "cfu" means colony foring units, "$OD_{600}$" means optical density measured at a wavelength of 600 nanometers, "SE" means standard error, "rpm" means revolutions per minute, "~" means approximately.

Example 1

Generation of a ZW801-4 Transposon-Based Knockout/Overexpression Library

A transposon-based genomic knockout/overexpression library was constructed in a xylose-utilizing recombinant strain of Z. mobilis to screen for acetate-resistant mutants. There were two principle reasons for using a transposon to generate the library. First, it is a completely unbiased approach that does not require any previous knowledge about the genes that play a role in acetate tolerance. Second, it is easy to identify the disrupted gene that is responsible for the desired phenotype since it is "tagged" with a selectable marker. The strain that was used to generate the library was ZW801-4. As described in detail in U.S. patent application No. 60/847,813, which is herein incorporated by reference, ZW801-4 was derived from ZW658 (ATCC # PTA-7858) through an intermediate strain, ZW800. The latter strain was constructed by double-crossover insertion from a suicide plasmid of a spectinomycin resistance cassette (Spec$^r$-cassette), flanked by wild type loxP sites, into the gene encoding glucose-fructose oxidoreductase (GFOR). The resulting GFOR knockout mutant was shown to have reduced production of xylitol, a detrimental by-product of xylose metabolism, and better production of ethanol during mixed sugar fermentation with glucose and xylose. ZW800 was then converted to ZW801-4 through Cre-mediated excision of the Spec$^r$-cassette. Elimination of the selectable marker left a single wild type loxP site in the middle of the GFOR open reading frame, which resulted in an in-frame stop codon that prematurely truncates translation of the protein. In addition, the GFOR coding sequence in ZW801-4 is missing ~72 bp of the original wildtype GFOR nucleotide sequence in the region surrounding the loxP site as a result of the design of the suicide construct. The sequence of the mutant GFOR coding region in ZW801-4 is given as SEQ ID NO:25. Like its immediate predecessor (ZW800), ZW801-4 does not generate any detectable xylitol since it does not produce a functional GFOR enzyme.

Figure 2:
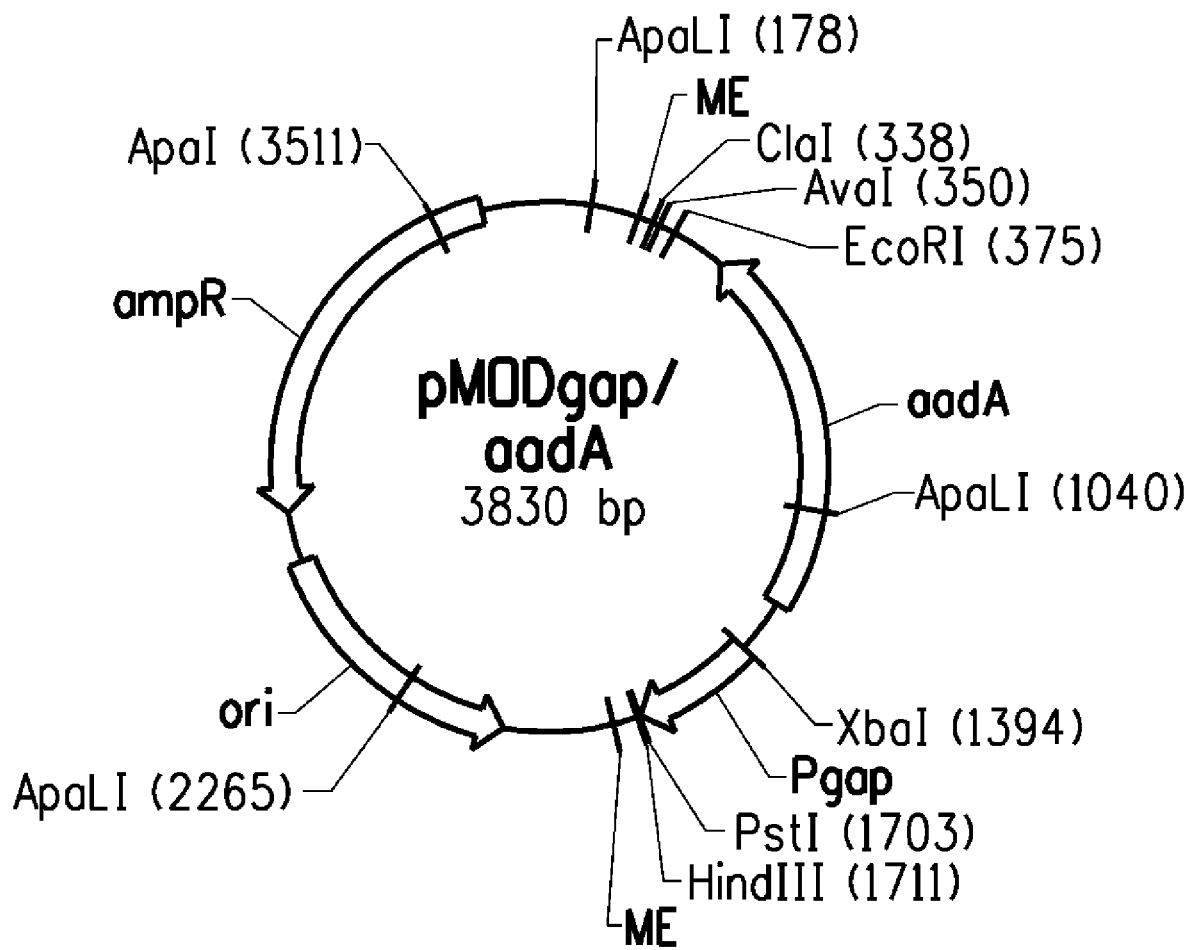
FIG. 2 shows a plasmid map of pMODgap/aada, the plasmid that was used to generate a transposon insertion library in ZW801-4.

The methodology that was used to generate the ZW801-4 genomic knockout/overexpression library was based on the Epicentre (Madison, Wis.) transposome technology using the pMOD™-2<MCS> Transposon Construction Vector (Cat. No. MOD0602). This plasmid includes an ampicillin resistance gene (ampR), an E. coli origin of replication (ori), and a multi-cloning site that is situated between the two mosaic ends (ME) that Tn5 transposase interacts with. For application in the present invention, pMOD™-2<MCS> was converted to pMODgap/aadA, shown in FIG. 2, by inserting a Spec$^r$-cassette (that has its own promoter) and the strong constitutive promoter for the Z. mobilis glyceraldehyde-3-phosphate dehydrogenase gene (Pgap) into the multi-cloning site that is situated between the two MEs; the Pgap promoter and Spec$^r$-cassette are oriented in opposite directions. Thus, the DNA fragment that was randomly inserted into the Z. mobilis chromosome during transposition using this construct contained both the Spec$^r$-cassette and Pgap promoter. The Pgap promoter was added to the transposon to increase the genetic diversity of the library, since it can potentially alter the expression of Z. mobilis chromosomal genes that are adjacent to the transposon insertion site.

The ZW801-4 genomic knockout/overexpression library consisted of ~17,500 independent mutants and the titer of the glycerol stock was ~7.1×10$^8$ Spec$^r$ colony forming units (cfu) per milliliter. This translates to ~1 transposon insertion event/ 115 nucleotides, which is about 8× coverage of the entire genome, based on random insertion of the transposon and ~2000 genes with an average size of 1 kb. Because of the low transformation frequency of Z. mobilis, it was expected that none or very few of the mutants would have more than one transposon insert.

Example 2

Screening the ZW801-4 Transposon-Based Knockout/Overexression Library for Mutants with Greater Tolerance for Acetate The ZW801-4 genomic knockout/overexpression library was screened for acetate-resistant mutants as described below. Before doing this, however, it was important to set up the proper selection conditions for the mutant enrichment process. The goal was to find a concentration of acetate that slowed the growth rate by at least a factor of two, but still allowed the cells to divide for several generations so that faster growing mutants could accumulate. It was also important to do this under process-relevant conditions in a concentrated mixture of glucose and xylose, since previous experiments have shown that osmotic stress and acetate both inhibit growth in a synergistic manner. Finally, controlling the pH was also critical since the real inhibitory compound is acetic acid, and the ratio of the protonated species to the non-protonated species would increase dramatically without pH control as the bacterial cells acidified the growth media. For example, if the pH were to drop from 5.8 to 4.8, the concentration of acetic acid would increase about 5-fold, since the p$K_A$ of this weak organic acid is ~4.8.

Figure 3:
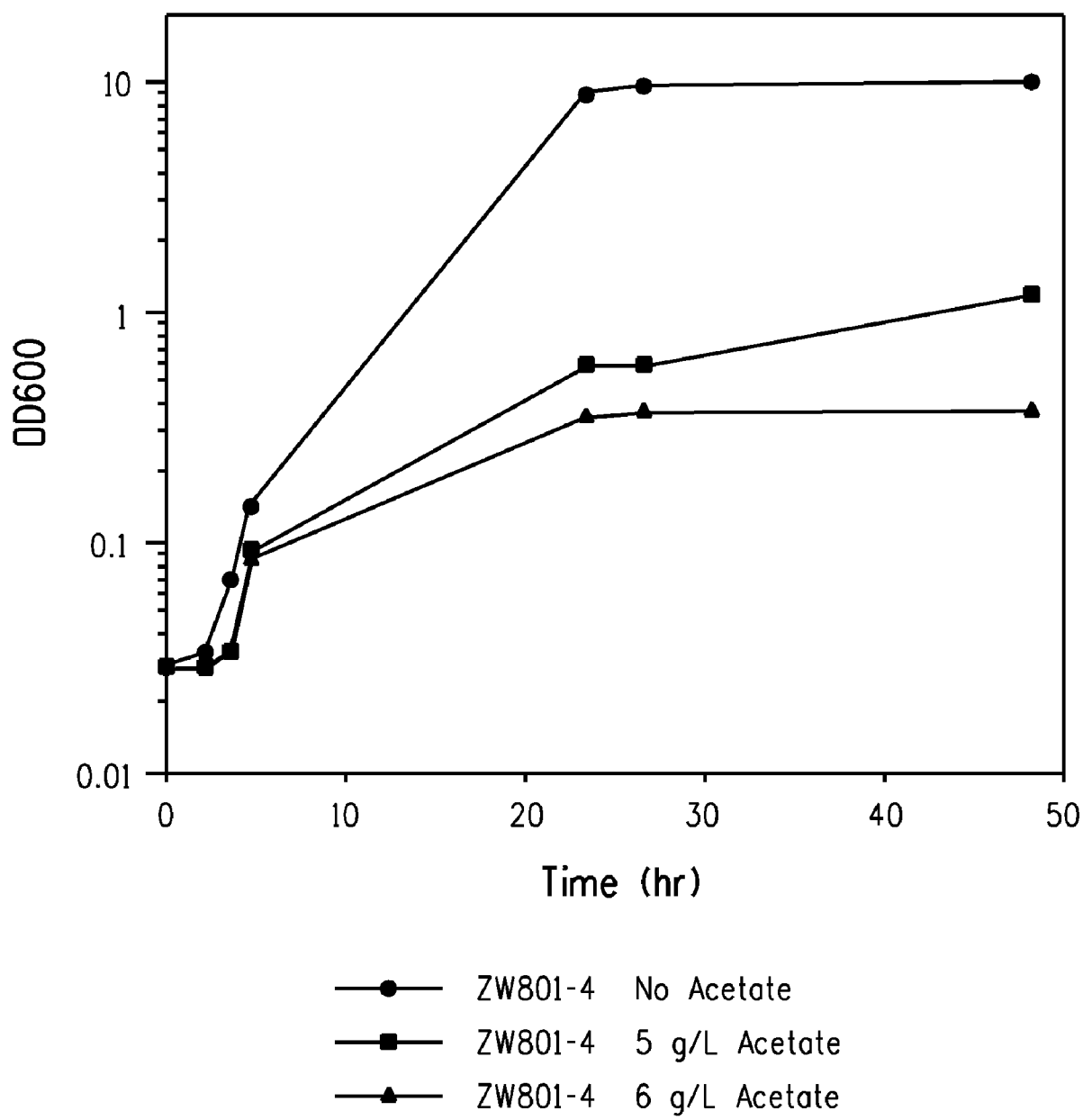
FIG. 3 shows a graph of growth of ZW801-4 in a concentrated mixture of glucose and xylose with two different amounts of acetate.

FIG. 3 shows the inhibitory effects of two different concentrations of acetate on the growth rate and final biomass yield of ZW801-4, the strain that was used to generate the library. Potassium acetate was used for these experiments and the final concentrations that are given below are based on the acetate component of the added salt in grams per liter. The pH-controlled bioreactors contained mRM3S media (10 g/L yeast extract, 2 g/L KH$_2$PO$_4$, 1 g/L MgSO$_4$, 5 mM sorbitol) plus 100 g/L glucose, 90 g/L xylose and 5 g/L or 6 g/L of acetate; pH and temperature were 5.8 and 30° C., and stirring was at 150 rpm. Based on the results shown in FIG. 3 and other experiments, 5 g/L of acetate was chosen for library screening, since this concentration of the inhibitor satisfied both criteria for growth as stated above.

To enrich for acetate-resistant mutants the following protocol was used. An aliquot (2 ml) of the library glycerol stock (OD$_{600}$=4.3; ~7.1×10$^8$ Spec$^r$ cfu/ml) was added to 20 ml of SM media (10 g/L yeast extract, 2 g/L KH$_2$PO$_4$, 1 g/L MgSO$_4$, 75 g/L glucose, 25 g/L xylose, initial pH 5.8) and the culture was incubated for 1.5 hours at 30° C. Following this recovery period, the cells were harvested by centrifugation and resuspended in 2.0 ml of the same growth media. An aliquot (10 µl) of the cell suspension (~7×10$^6$ Spec$^r$ cfu) was then inoculated into 15 ml of mRM3S media that contained 100 g/L glucose, 90 g/L xylose, and 4 g/L potassium bicarbonate to help minimize pH changes; the initial pH was adjusted to 5.8 with concentrated phosphoric acid before the cells were added and the initial OD$_{600}$ was ~0.0025. This was the seed culture that was used for the mutant enrichment procedure. It was grown at 30° C. to OD$_{600}$ of ~0.5 and then 7.5 ml was inoculated into a pH-controlled bioreactor. The 150-ml final culture contained mRM3S media plus 100 g/L glucose, 90 g/L xylose, 5 g/L of acetate, and the pH was maintained at 5.8 by automated KOH addition. After ~24 hours of growth at 30° C., an aliquot of the culture (OD$_{600}$~0.5) was transferred to a new bioreactor that contained fresh growth media with the same composition to an initial OD$_{600}$ of ~0.02. This step was repeated six more times essentially as described above. In general, the cells were transferred every 24-36 hrs and the initial OD in the bioreactor was ~0.02 to ~0.03. Thus, there were at least five generations between transfers. After the seventh round of mutant enrichment procedure, a glycerol stock of the culture was prepared for further characterization.

Figure 4A:
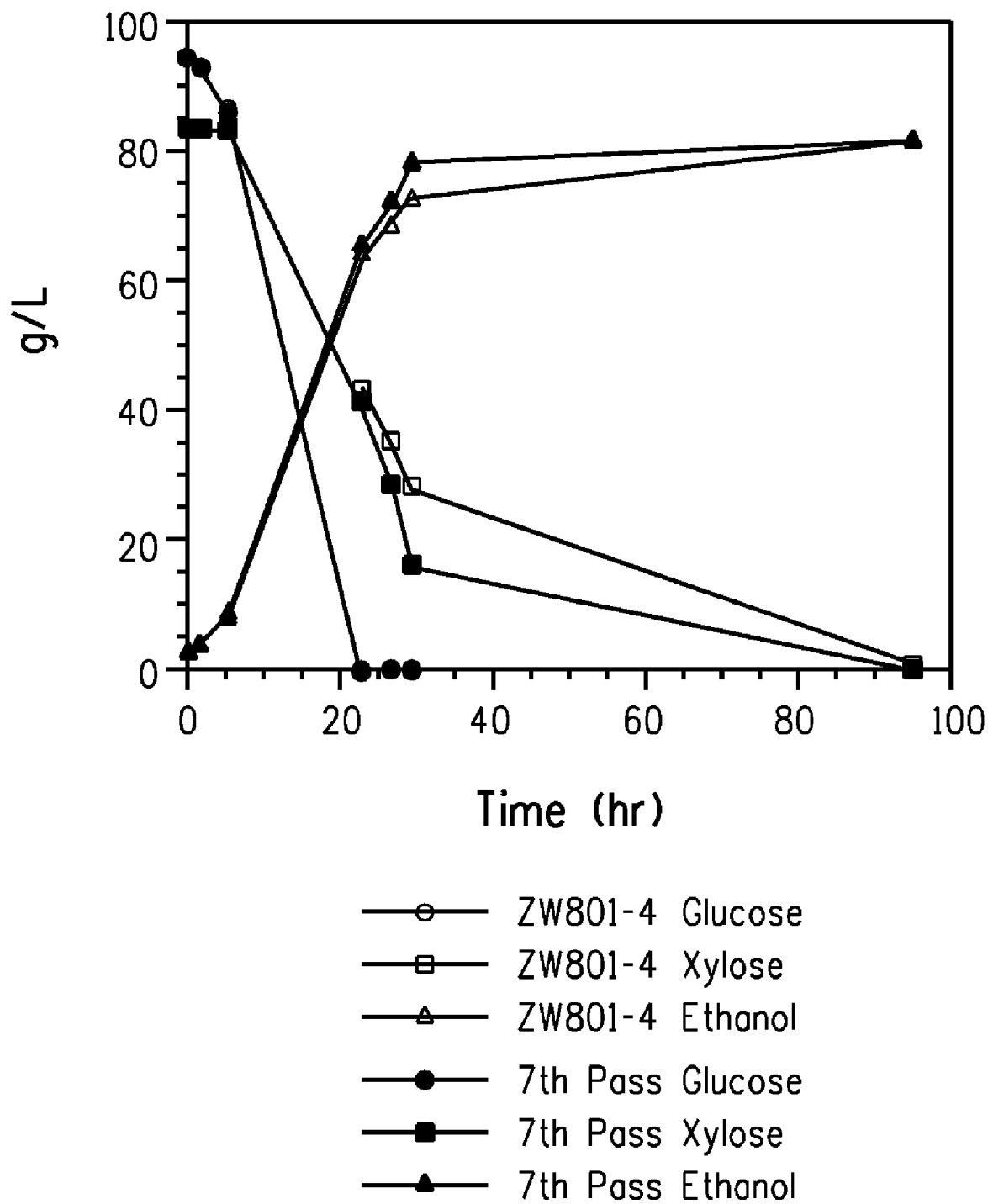

FIG. 4A shows the results of a pH-controlled bioreactor experiment with high sugar and acetate that was performed with the enriched mutant culture after the seventh transfer. The control for this experiment was the parent strain, ZW801-4. Seed cultures were grown at 30° C. in SM media to an OD$_{600}$ of ~4.5 and the bioreactors were started with a 10% inoculum. The final 150-ml cultures contained mRM3S media plus 100 g/L glucose, 90 g/L xylose and 6 g/L acetate. Stirring was at 150 rpm, and pH and temperature were maintained at 5.8 and 30° C., respectively. At various times 1.0-ml aliquots of the cultures were removed for HPLC analysis using an HP 1100 equipped with a refractive index detector (Hewlett-Packard, Palo Alto, Calif.) to determine the concentrations of glucose, xylose, and ethanol that were present in the fermentation broth. Prior to HPLC analysis, cells were removed by centrifugation and the supernatant was filtered through a 0.22 μm cellulose acetate Spin-X centrifuge tube filter (Costar, catalog number 8160) to remove small particles. Compounds were separated on an Aminex HPX-87H column (Bio-Rad) that was run at 55° C. under isocratic conditions using a flow rate of 0.6 ml/min and 0.01 NH$_2$SO$_4$ as the mobile phase. Authentic standards of known concentration were used to quantify the peaks of interest and the results were expressed in g/L.

The results given in FIG. 4A show that the enriched mutant library culture had faster utilization of xylose and more rapid production of ethanol during the late stage of fermentation. Note that this occurred after all of the glucose was depleted and the ethanol concentration was approaching toxic levels. Nevertheless, by the end of the experiment both cultures had consumed all the sugar and produced the same amount of ethanol. When this experiment was repeated using a slightly higher concentration of sugar (105 g/L glucose and 100 g/L xylose) and more acetate (9 g/L), a similar phenomena was observed (FIG. 4B), thus demonstrating that the results were reproducible.

Example 3

Genetic Characterization of Mutant Strains

Figure 4B:
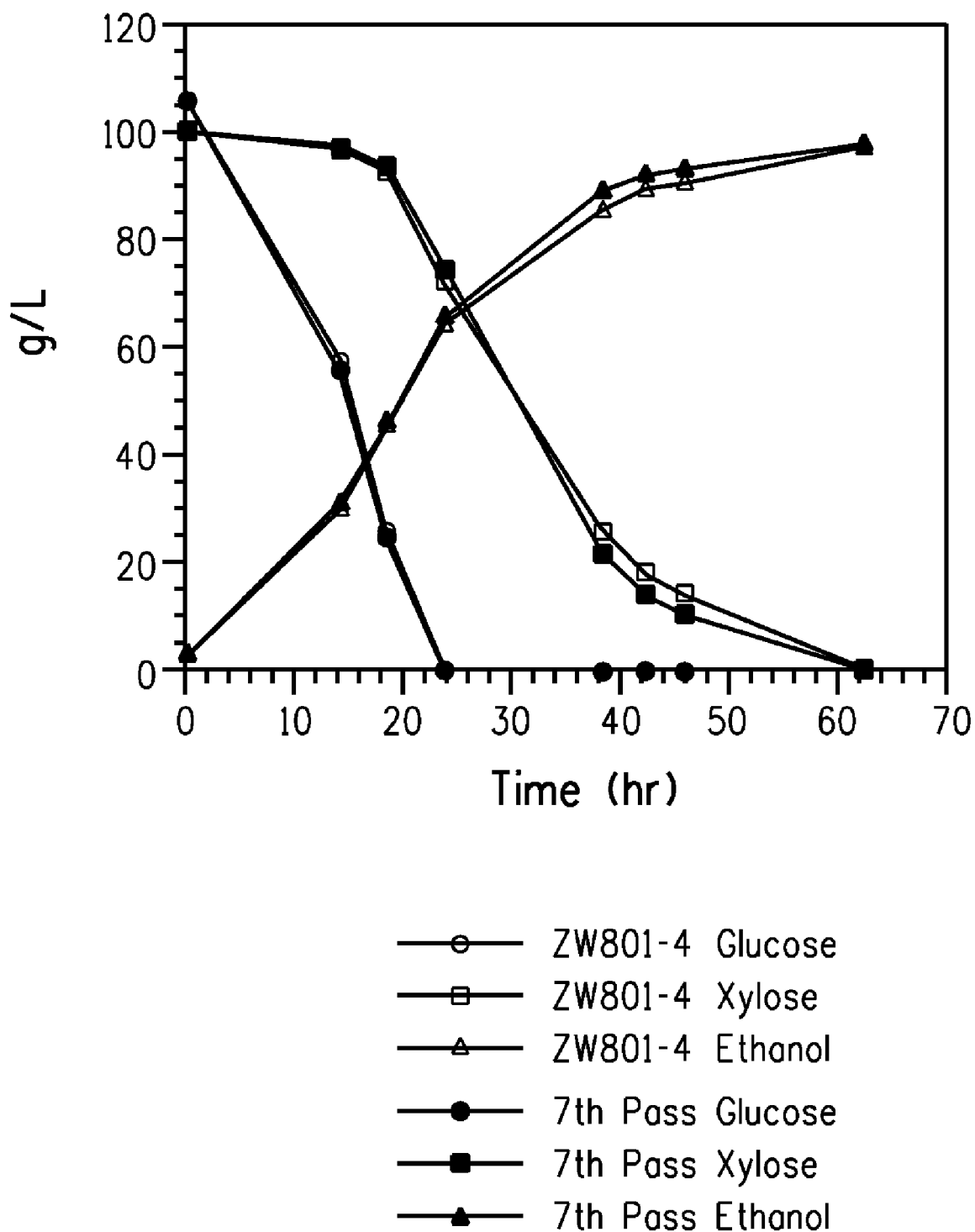

To see what types of mutants were enriched for during the selection process, single colonies were isolated from the library culture during the second bioreactor experiment (FIG. 4B). An aliquot of the culture was removed at the 24-hr time point and the cells were grown on agar plates that contained MMG media (50 g/L glucose, 10 g/L yeast extract, 5 g/L of tryptone, 2.5 g/L of (NH$_4$)$_2$SO$_4$, 0.2 g/L K$_2$HPO$_4$, and 1 mM MgSO$_4$). Following a 48-hr incubation period at 30° C. under anaerobic conditions, seventeen of the resulting colonies were randomly selected for DNA sequence analysis to determine the site(s) of transposon insertion. The following procedure was used for this analysis. The colonies were diluted in 50 μl of water and genomic DNA was amplified using the GenomiPHI Amplification Kit (GE Healthcare Life Sciences Cat. No. 25-6600-1). Briefly, 1 μl of the cell suspension was added to 9 μl of the Lysis Reagent and the mixture was heated to 95° C. for 3 min and immediately cooled to 4° C. Next, 9 μl of Enzyme Buffer and 1 μl of Phi 29 DNA polymerase were added to the lysed samples. After 18 hours of amplification at 30° C., the polymerase was heat-inactivated for 10 min at 65° C. and the sample was then immediately cooled to 4° C.

An aliquot of the amplified sample (8 μl) was then added to 16 μl of BigDye v3.1 Sequencing Reagent (PN #4337457 Applied Biosystems, Foster City, Calif.), 1 μl of Thermofidelase (Fidelity Systems, Gaithersburg, Md.), 12 μl of Molecular Biology Grade water (Mediatech, Inc., Herndon, Va.), and 3 μl of 10 μM primer: either SpecT-FOR (SEQ ID No:2: GTGAAAGGCGAGATCACCAAGGTAGTC) or SpecT-Rev (SEQ ID No:3: CTACCTCTGATAGTTGAGTCGATACTTCGG). Note that both of these primers hydridize to the Spec$^r$-cassette that is part of the transposon that was used to generate the ZW801-4 genomic knockout library, but they are oriented in opposite directions. The sequencing reactions were then thermal cycled as follows: 3 min at 96° C. followed by 200 cycles of (95° C. 30 sec+55° C. 20 sec+60° C. 2 min) and stored at 4° C. Prior to sequencing, the unincorporated ddNTPs were removed using Edge Biosystems (Gaithersburg, Md.) clean-up plates. The entire 40-μl sequencing reaction mixture was pipetted into one well of a pre-spun 96-well clean up plate, and the plate was spun for 5 min at 5000× gravity in a Sorvall RT-7 refrigerated centrifuge. The cleaned up reactions were then placed directly onto an Applied Biosystems 3730 DNA sequencer and sequenced with automatic base-calling.

Remarkably, all 17 colonies that were sequenced had a transposon inserted in the himA open reading frame (reverse complement of nucleotides #1138224 through #1138565 of the Z. mobilis genome (GenBank accession number AE008692)), and three different insertion events were identified. Eleven of the colonies (including AcR#3, see below) had a transposon insert at nt #1138413, four of the colonies had an insert at nt #1138267, and two of the colonies had a insert at nt #1138508. Thus, all three insertion events occurred within a 250 bp stretch of DNA. The fact that 65% of the himA knockout mutants had a transposon insert at nt #1138413 after the seventh round of the mutant enrichment procedure suggested that this event may have conferred faster growth or greater survivability than the other two insertion events. There was also another interesting observation from the sequence analysis. Although in theory a Tn5 transposon can insert itself into DNA in either direction, all three insertion events that were recovered from the selection process had the same orientation with the Pgap promoter pointing in the opposite direction of the himA open reading frame.

It is clear from the sequencing results described above that the experiments that are shown in FIG. 4 were performed with a mixed population of cells, not a purified strain. Thus, AcR#3 was chosen for further characterization of the himA phenotype since this strain has a transposon insert at nt #1138413, which was the most frequently isolated event.

Example 4

Effect of himA Gene Inactivation on Acetate Tolerance and Fermentation Performance Under Process-Relevant Conditions AcR #3 is More Resistant to Acetate than ZW801-4

The growth media that was used for the mutant selection process contained high concentrations of glucose and xylose, in addition to an inhibitory level of acetate. It was therefore possible that the improved fermentation performance that was observed after the seventh round of enrichment (FIG. 4) was related to osmotic stress or better growth on xylose, since this sugar is not utilized as well as glucose. It was also possible that ethanol resistant mutants had been enriched for since they too would presumably grow faster or survive longer under the experimental conditions employed. To rule out these other possibilities and see if himA gene inactivation really does confer higher tolerance to acetate, strain AcR#3 was compared to the parent strain, ZW801-4 under the following conditions. The experiment was performed at 33° C. in shake flasks (20 ml cultures in 50 ml tubes), and the growth media contained 10 g/L yeast extract, 2 g/L KH2PO$_4$, 1 g/L MgSO$_4$, 10 mM KHCO$_3$ (to help maintain pH), 50 g/L glucose and 0, 8, or 12 g/L acetate, which was added as the potassium salt; the concentrations of acetate that are given are based on the acetate component of the potassium salt. The initial pH was adjusted to 5.8 with phosphoric acid before the cells were added and the cultures were gently agitated on a recipricol shaker (150 rpm). The seed cultures were grown to late exponential phase ($OD_{600}$~1.4) in the same media without acetate and the initial $OD_{600}$ for the experimental cultures was 0.03. It is important to note that these are ideal conditions for growth of Z. mobilis in the absence of acetate, since there is no osmotic stress and the preferred substrate glucose is the carbon source. Furthermore, the highest concentration of ethanol that could be generated in this experiment is <25 g/L which has little or no effect on growth of Z. mobilis.

Figure 5A:
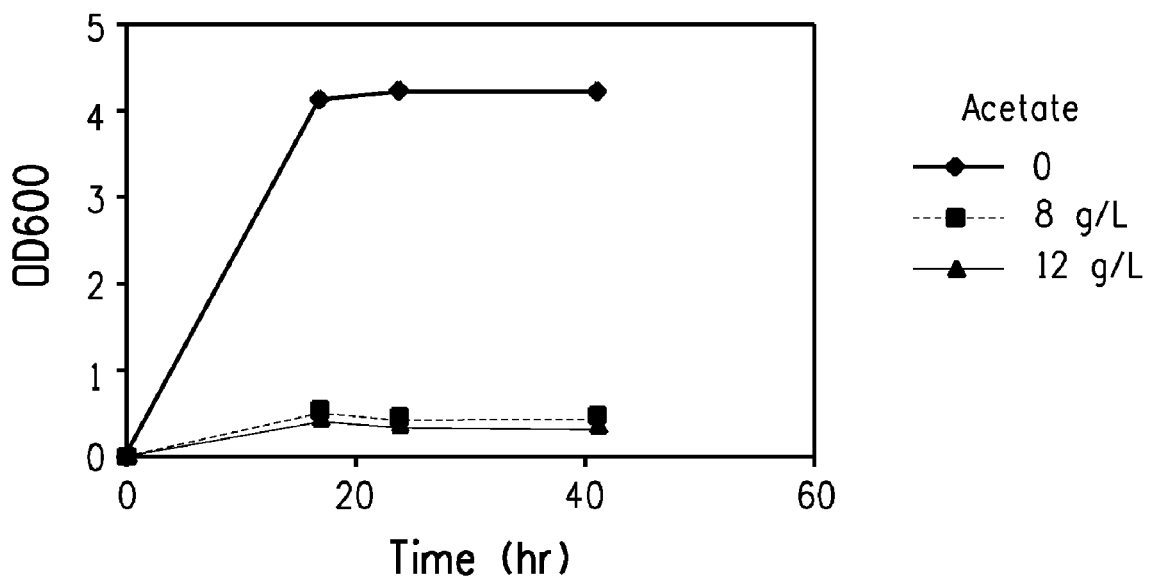
Figure 5B:
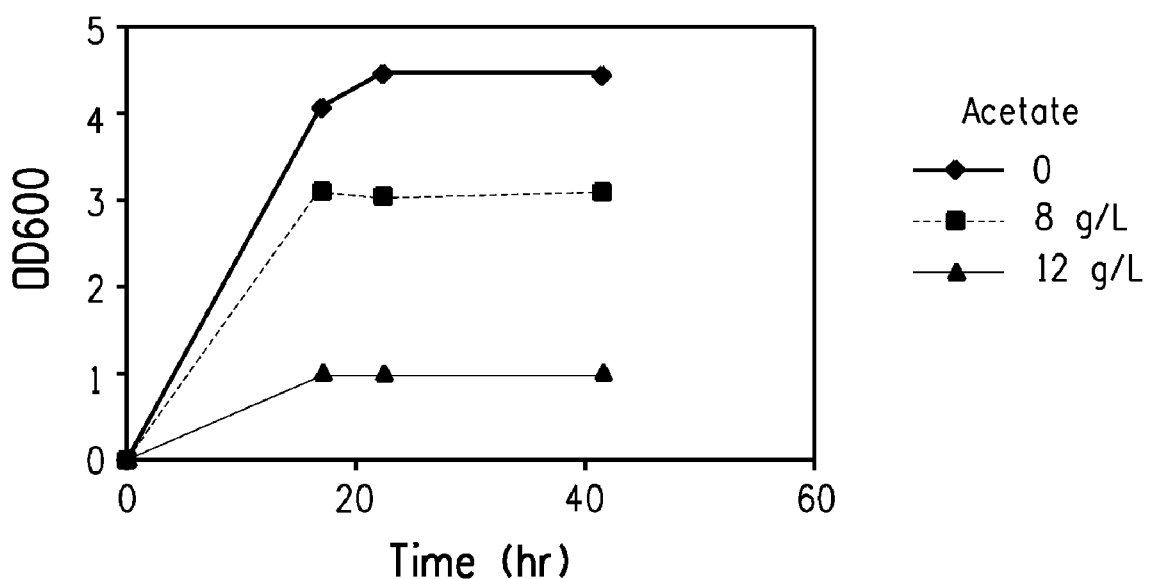

In the absence of acetate, AcR#3 and ZW801-4 grew with similar kinetics and produced the same amount of biomass as judged from the final $OD_{600}$ values as shown in FIG. 5. The AcR#3 strain (FIG. 5B), however, had a much greater tolerance for acetate than the parent strain (FIG. 5A). For example, growth of ZW801-4 was almost completely abolished by 8 g/L of acetate, while this concentration of the inhibitor had a negligible effect on AcR#3. Indeed, the himA knockout mutant was more resistant to 12 g/L of acetate than ZW801-4 was to 8 g/L of acetate. This experiment was repeated and the same results were obtained. It is important to recall that acetate is much more inhibitory when the pH of the growth media is not controlled like it was in the bioreactor experiments that are shown in FIG. 4. In shake flask experiments without pH control, the cells acidify the growth media and the ratio of acetic acid/acetate increases dramatically, and it is the protonated species that inhibits bacterial growth as already noted.

Figure 6A:
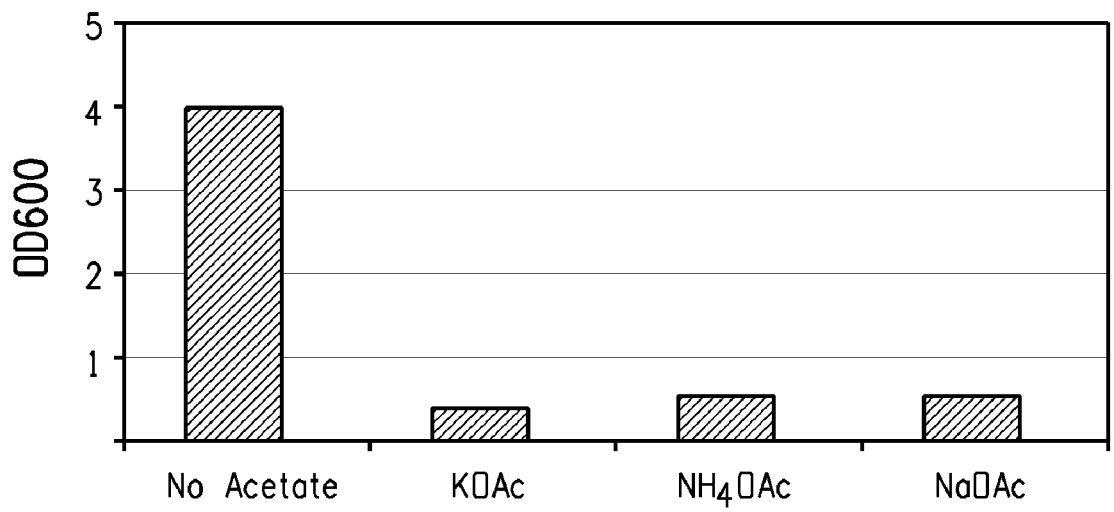
Figure 6B:
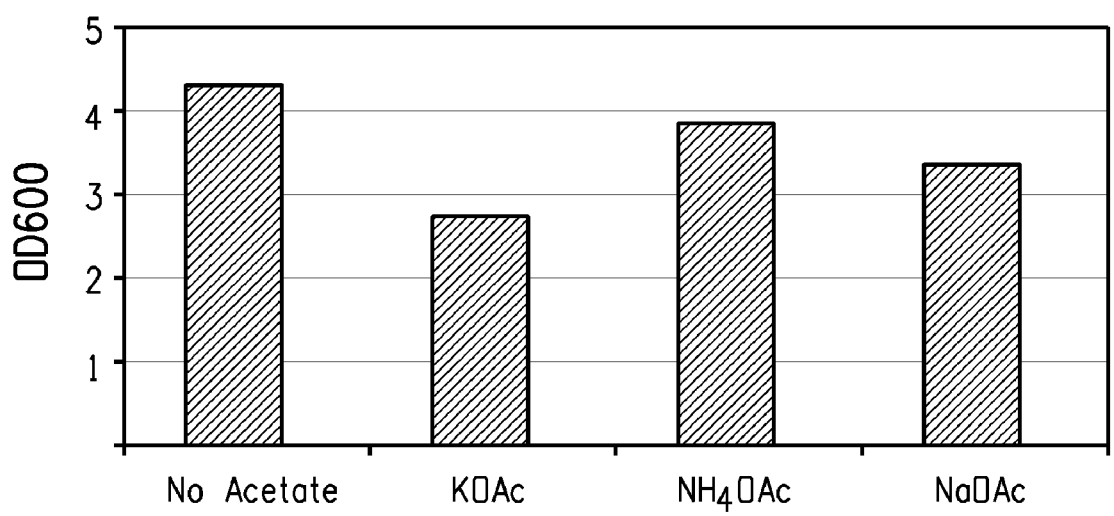

Since potassium ions could have at least partially contributed to the inhibition of growth that was observed for both strains in the above experiment, it was important to test other sources of acetate. The conditions that were used for this set of experiments were identical to those described above, but sodium acetate and ammonium acetate were also included in the analysis. The concentration of the acetate anion was 8 g/L (as defined above) in all cases. Shown in FIG. 6 are the final $OD_{600}$ values for the various cultures at the 43-hr time point. ZW801-4 (FIG. 6A) was strongly inhibited by 8 g/L of acetate, regardless of the acetate salt that was used. This observation clearly indicates that the principle inhibitor in these experiments was acetic acid, and that the monovalent cations in the acetate salts had little or no effect on growth at the concentrations that were used. Although all three acetate salts also had a negative impact on growth of AcR#3 (FIG. 6B) the inhibition with this strain was not that dramatic when the concentration of acetate was only 8 g/L. Taken together, the experiments that are shown in FIGS. 5 and 6 provide unequivocal evidence that AcR#3 is much more resistant to acetate than the parent strain, ZW801-4.

AcR #3 Performs Better in a High Sugar Plus Acetate Mixture than ZW801-4

When AcR#3 was tested under the same experimental conditions that were used for the "mixed population" of mutants (FIG. 4B), it outperformed ZW801-4 and there was a much bigger difference between the two cultures than there was in the earlier experiment (FIG. 7). Consistent with the previous results, the improvement was only evident during the late stage of fermentation after all the glucose had been consumed and xylose was the only remaining carbon source. Indeed, close inspection of the time courses that are shown in FIG. 7 revealed that the initial rates of glucose utilization and ethanol production were slightly slower for AcR#3. However, after all of the glucose was gone, it is clear from the slopes of the xylose utilization curves that AcR#3 was able to convert this sugar to ethanol at a faster rate than ZW801-4 during the late stage of fermentation.

The full potential of AcR#3 could not be evaluated in the experiment described above since even the control strain was able to use all of the sugar by the end of the experiment under the conditions employed. To remove this limitation, AcR#3 and ZW801-4 were tested again using conditions that were more demanding. The temperature was elevated from 30° C. to 33° C. and a higher concentration of glucose and xylose was used. The seed cultures were grown at 30° C. in SM media to an $OD_{600}$ of ~4.4 and a 10% inoculum was used to start the bioreactors. The final 150 ml cultures contained mRM3S media plus 126 g/L glucose, 107 g/L xylose and 10 g/L acetate. The stirrer was set at 150 rpm, and pH and temperature were maintained at 5.8 and 33° C., respectively. This experiment was conducted in triplicate for ZW801-4 and in duplicate for AcR #3, and the endpoint values (67-hr time points) for glucose, xylose, acetate and ethanol (Mean±SE) are given in Table 1. HPLC analysis of the fermentation broth was as described in Example 2 and concentrations for all compounds in the table are in g/L. Under these harsher conditions AcR#3 consumed ~10% more xylose and produced ~4% more ethanol than the parent strain, ZW801-4.

TABLE 1

Endpoint values for xylose, ethanol and xylitol in pH-controlled fermenters with ZW801-4 and Acr#3 strains grown in high sugar and acetate.

| Strain | Glucose | Xylose | Acetate | Ethanol |
|---|---|---|---|---|
| ZW801-4 | 0 | 27.1 ± 1.4 | 10.8 ± 0.1 | 90.3 ± 0.3 |
| AcR#3 | 0 | 18.7 ± 0.4 | 10.8 ± 0.1 | 93.8 ± 0.2 |

AcR #3 Performs Better than ZW801-4 in 100% Mock Hydrolysate

Performances of AcR#3 and ZW801-4 were evaluated in the presence of concentrations of ammonium and acetate ions that are expected to be present in biomass hydrolysate produced using an ammonium hydroxide pretreatment process. This was a critical experiment since it has been estimated that the concentration of ammonium ions during fermentation of ammonium hydroxide pretreated corn stover hydrolysate may exceed 180 mM, and high concentrations of ammonium ions inhibit growth of Z. mobilis (Agrawal (1989) Biotechnology and Bioengineering 34: 278-281). The synthetic 100% Mock Hydrolysate (100% MH) medium that was used for these experiments contains 5 g/L yeast extract, 15 mM $(NH_4)_2HPO_4$, 160 mM ammonium acetate, 1 g/L MgSO$_4$ and 10 mM sorbitol (pH 5.8). Thus, the final concentrations of acetate and ammonium ions in 100% MH after addition of the seed cultures were ~9.5 g/L and 190 mM, respectively. The experiments were conducted in pH-controlled bioreactors. The seed cultures were grown at 30° C. in SM media to an $OD_{600}$ of ~4.4 and a 10% inoculum was used to start the bioreactors. The final 150-ml cultures contained 100% MH plus 110 g/L glucose and 90 g/L xylose. The stirrer was set at 150 rpm, and pH and temperature were maintained at 5.8 and 33° C., respectively. At various times, aliquots were removed for HPLC analysis of the fermentation broth using the same procedure that is described in Example 2. The results from a representative pair of experiments that were conducted at the same time are shown in FIG. 8: ZW801-4 in 8A, and AcR#3 in 8B.

Consistent with previous observations, the AcR#3 strain did not have an increased rate of ethanol production when glucose was the only sugar that was being metabolized. However, the superior performance of AcR#3 was very evident during the late stage of fermentation when xylose was the only remaining carbon source. By the time ZW801-4 had consumed all of the glucose, the ethanol concentration was already >65 g/L, which is a bactericidal concentration even for Z. mobilis. Adding to this harsh environment were the high concentrations of acetate and ammonium ions, which both potentiate ethanol toxicity. As the ethanol level continued to rise, xylose metabolism got slower and slower, and eventually came to a grinding halt. The same scenario occurred with AcR#3, but the timeframe was extended. Because AcR#3 is more resistant to acetate it was able to survive longer in the toxic environment, and was therefore able to consume virtually all the xylose in the growth media and produce more ethanol than ZW801-4.

The experiment with 100% MH was repeated two more times for both strains and the results were virtually identical. A statistical analysis of the three experiments is given in Table 2 using endpoint values (48-hr time point) for glucose, xylose, acetate and ethanol; all concentrations are in g/L (Mean±SE). Each of the six bioreactors was inoculated with an independently-grown seed culture. In 100% MH, AcR#3 consumed ~14 g/L more xylose than ZW801-4 and this increased the final ethanol titer from 82 g/L to 91 g/L, which is more than a 10% increase. These results are even more dramatic than those obtained in the high sugar plus acetate experiments given in Table 1. When ammonium ions are present in the growth media with acetate, the stress level is elevated to an even higher level and the benefits of himA gene inactivation become more obvious. Clearly, a strain like AcR#3 that has higher tolerance for acetate is better equipped to contend with the other inhibitors in its environment, like ethanol and ammonium ions.

TABLE 2

End-point values for glucose, xylose, ethanol, and acetate in pH-controlled fermentors with ZW801-4 and AcR#3 strains grown in 100% Mock Hydrolysate.

| Strain | Glucose | Xylose | Acetate | Ethanol |
|---|---|---|---|---|
| ZW801-4 | 0 | 15.6 ± 3.9 | 11.5 ± 0.5 | 81.9 ± 2.8 |
| AcR#3 | 0 | 1.0 ± 0.2 | 10.7 ± 0.4 | 91.3 ± 0.7 |

Example 5

Generation of a Suicide Construct for Knockout of the himA Gene in ZW801-4

Although the results presented thus far strongly suggest that the acetate-resistant phenotype of AcR#3 resulted from disruption of the himA gene, two other factors could potentially have contributed. As described in Example 1, the transposon that was used to generate the ZW801-4 genomic knockout/overexpression library contained a Spec$^r$-cassette and the Z. mobilis Pgap promoter. These elements are oriented in opposite directions, and both of them were inserted into the himA open reading frame during transposition. Since the Z. mobilis Pgap promoter is a strong, constitutive promoter it could have altered the expression level of genes that are in close proximity to the himA transposon insertion site. It is also conceivable that at least part of the acetate-resistant phenotype of AcR#3 resulted from spontaneous mutations in other genes that may have also allowed faster growth during the library mutant-enrichment process (Example 2). To rule out these possibilities and see if himA gene inactivation is solely responsible for the higher acetate tolerance of AcR#3, we designed a suicide construct to knockout the himA gene in ZW801-4. This non-replicating plasmid has a spectinomycin-resistance cassette but does not contain a Pgap promoter as described in more detail below.

The suicide construct that was used in the present invention to knockout the himA gene in ZW801-4 ("pHimA") was ultimately derived from another suicide construct ("pLDHSp-9WW") that was previously used to insertionally-inactivate the D-lactate dehydrogenase gene in Z. mobilis using host-mediated, double-crossover, homologous recombination and spectinomycin resistance as a selectable marker. pLDHSp-9WW was also derived from a number of other constructs that were previously generated. The initial precursor for all of these constructs was the plasmid vector pNEB193 (New England Biolabs #N3051S) that is commercially available. This plasmid was chosen because it can replicate in E. coli but it cannot replicate in Z. mobilis. All of the steps and intermediates that were involved in generation the himA knockout construct are described below in chronological order starting with plasmid pNEB193.

Construction of PLDH193 pNEB193 was double-digested with SbfI and AscI for insertion of the DNA fragment that is described below. Both restriction sites are unique and are located in the multi-cloning region of the plasmid. The SbfI/AscI-linearized pNEB193 plasmid DNA fragment was purified using Qiagen's QIAQuick Purification Kit (catalog #28104) according to the manufacturer's protocol. The DNA insert that was cloned into pNEB193 was a 2268 bp fragment that was PCR-amplified from Z. mobilis genomic DNA that was isolated from strain ZW1 (ATCC #31821) using Qiagen's Blood & Cell Culture Maxi Kit (catalog #13362). The synthetic oligonucleotides that were used for PCR-amplification of this fragment were Primers 1 and 2.

```
                                           (SEQ ID NO: 4)
Primer 1   CTACTCATTTcctgcaggTGGTAACTCATTGCGCGCTC (SEQ ID NO: 5)
Primer 2   CATCTTACTggcgcgccAAAAATCTGCGGCTGACATAC
```

The underlined bases of Primer 1 (forward primer) hybridize to nucleotides 1262739-1262720 of the Z. mobilis genome (GenBank accession number AE008692) at the 3' end of the open reading frame that codes for phosphoglyceromutase (pgm), while the lower case letters correspond to an SbfI site that was added to the 5' end of the primer. The underlined bases of Primer 2 (reverse primer) hybridize to nucleotides 1260490-1260472 of the Z. mobilis genome, which is just upstream from the open reading frame that codes for alcohol dehydrogenase I (adhI), while the lower case letters correspond to an AscI site that was added to the 5' end of the primer. The 2268 bp DNA fragment that was the target for PCR-amplification therefore consists of the following elements starting from the SbfI site and ending at the AscI site: (a) the 3' end of the pgm gene, (b) the entire ldh gene that codes for D-lactate dehydrogenase, and (c) a 5' non-translated region of the adhI gene. The PCR product was cut with SbfI and AscI, and the resulting DNA fragment was ligated into the SbfI/AscI-linearized pNEB193 vector that was described above. The ligation reaction mixture was used to transform *E. coli* JM110 and the transformed cells were plated on LB media that contained ampicillin (100 µg/ml). Ampicillin-resistant tranformants that contained plasmids with the correct size insert were initially identified by PCR using resuspended colonies ("colony PCR") and Primers 1 and 2. Subsequent confirmation of positive clones came from restriction digestion analysis of plasmid DNA with SbfI and AscI, and DNA sequence analysis of the 2268 bp fragment that was generated by colony PCR with the ampicillin-resistant transformants. The plasmid that was selected for further manipulation was named PLDH193.

Construction of pLDHTc139#7

Plasmid pLDH193 has a unique NcoI site that is located in about the middle of the ldh open reading frame. This site was used to insert a DNA fragment that confers resistance to tetracycline. The tetracycline resistance cassette (Tc$^r$-cassette) that was used for this manipulation was generated by PCR using plasmid pACYC184 (GenBank accession number X06403) as a DNA template and Primers 3 and 4 as PCR primers.

Figures 9A, 9B:
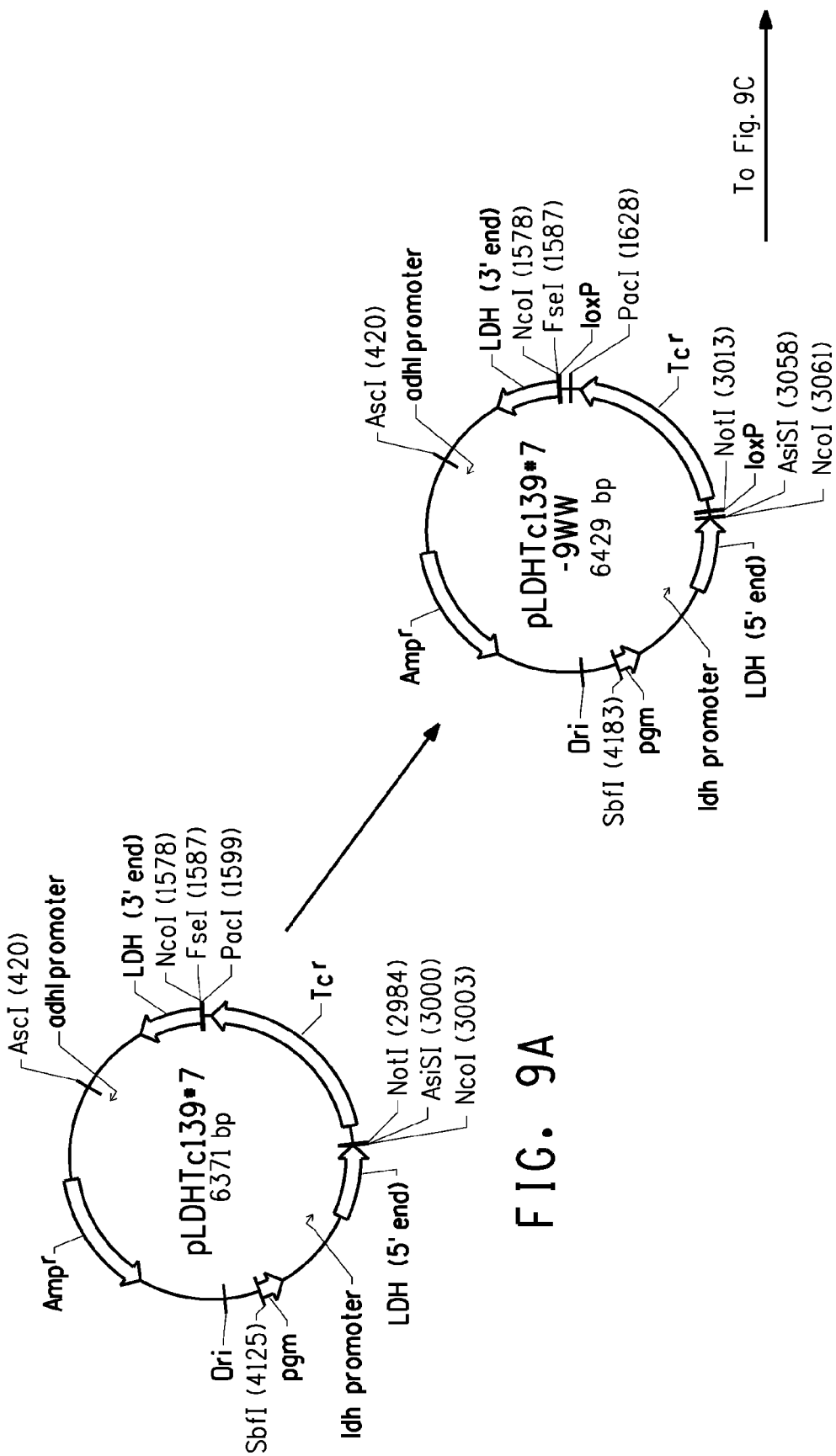

Primer 3 (SEQ ID NO: 6):
ACTCATTTccatggCGATCGCACTAT*gcggccgc*AATGTAGCACCTGAAG
TCAGCC Primer 4 (SEQ ID NO: 7):
ATCTCACTccatggCCGGCCAACTA*ttaattaa*GAATTGATTGGCTCCAA
TTCTTG The bold underlined bases of Primer 3 (forward primer) hybridize just upstream from the promoter for the tetracycline resistance gene. Primer 3 also has three restriction sites (NcoI, AsiSI, and NotI) that were added to its 5' end. The NcoI site is in normal lower case letters. The AsiSI site is underlined with a thin line. The Not I site is in italicized lower case letters. The bold underlined bases of Primer 4 (reverse primer) hybridize just downstream from the stop codon for the tetracycline resistance gene, and this primer also has three restriction sites (NcoI, FseI, and PacI) that were added to its 5' end. Similar to the labeling above, the NcoI site is in normal lower case letters, the FseI site is underlined with a thin line, and the PacI site is in italicized lower case letters. The 1448 bp Tc$^r$-cassette that was generated with Primers 3 and 4 was cut with NcoI and purified by preparative agarose gel electrophoresis. The resulting DNA fragment was then ligated into the unique NcoI site that is present in the ldh open reading frame of plasmid, pLDH193. To minimize the possibility of re-circularization of the vector without an insert, the NcoI-digested pNEB193 was dephosphorylated with calf intestinal alkaline phosphatase prior to ligation. The ligation reaction mixture was introduced into *Escherichia coli* JM110 and the transformed cells were plated on LB media that contained 20 µg/ml of tetracycline. Tetracycline-resistant tranformants that contained plasmids with the correct insert were identified by restriction digest analysis with NcoI, AsiSI, NotI, FseI, and PacI, and the orientation of the Tc$^r$ cassette was confirmed by PCR analysis using appropriate primers. A circle diagram of the plasmid that was selected for further manipulation (named pLDHTc139#7) is shown in FIG. 9A. In another project, this suicide construct was successfully used for insertional-inactivation (to "disrupt" or "knockout") of the D-lactate dehydrogenase gene in ZW1 using host-mediated, double-crossover, homologous recombination and growth on tetracycline as the selectable marker.

Construction of pLDHTc139#7-9WW

Having demonstrated that pLDHTc139#7 could be used to "knockout" the D-lactate dehydrogenase gene in ZW1, the construct was then modified so that it would be possible to remove the selectable marker from the chromosome after gene disruption, using Cre recombinase. To accomplish this goal, two wild type loxP sites (Lee and Saito, 1998) were added to pLDHTc139#7 taking advantage of the four unique restriction sites that flank the Tc$^r$-cassette, namely, AsiSI and NotI at the 5' end and PacI and FseI at the 3' end. The first loxP site was inserted between the AsiSI and NotI sites of plasmid pLDHTc139#7 after cutting the construct with both enzymes and purifying the resulting large DNA fragment. The loxP site that was inserted into this location was generated from two synthetic oligonucleotides (Oligos 5 and 6) that were both phosphorylated at their 5' end.

Oligo 5 (SEQ ID NO: 8):
cgcATAACTTCGTATAATGTATGCTATACGAAGTTATgc

Oligo 6 (SEQ ID NO: 9):
ggccgcATAACTTCGTATAGCATACATTATACGAAGTTATgcgat

Oligos 5 and 6 are complimentary to each other, and when annealed together form a full-length double-stranded wild type loxP site that has single-stranded overhangs at both ends, which allow the DNA fragment to be ligated between the AsiSI and NotI sites of pLDHTc139#7. The upper case letters in Oligos 5 and 6 correspond to the full-length wild type loxP site, while the lower case letters indicate the nucleotides that were used to ligate the double-stranded DNA fragment into the AsiSI and NotI sites of pLDHTc139#7.

The ligation reaction mixture was used to transform *Escherichia coli* DH10B and the transformed cells were plated on LB media that contained 20 µg/ml of tetracycline. Tetracycline-resistant tranformants that contained plasmids with the loxP site correctly inserted into the AsiSI and NotI sites of pLDHTc139#7 were identified by restriction digest analysis, colony PCR using appropriate primers, and DNA sequence analysis of the relevant regions. The plasmid that was selected for further manipulation was named pLDHTc139#7-9W.

Next, a second wild type loxP site was inserted between the PacI and FseI sites at the other end of the Tc$^r$-cassette in pLDHTc139#7-9W, after cutting the plasmid with both enzymes and purifying the resulting large vector fragment. The loxP site that was inserted into this location was also generated with two synthetic oligonucleotides (Oligos 7 and 8) that were both phosphorylated at their 5' end.

Oligo 7 (SEQ ID NO: 10):
taaATAACTTCGTATAATGTATGCTATACGAAGTTATggccgg

Oligo 8 (SEQ ID NO: 11):
ccATAACTTCGTATAGCATACATTATACGAAGTTATttaat

Oligos 7 and 8 are complimentary to each other, and when hybridized form a full-length, double-stranded wild type loxP site that has single-stranded overhangs at both ends that allow the DNA fragment to be ligated between the PacI and FseI sites of pLDHTc139#7-9W. The upper case letters in Oligos 7 and 8 correspond to the full-length loxP site, and the lower case letters indicate the nucleotides that were used to ligate the double-stranded DNA fragment into the PacI and FseI sites of pLDHTc139#7-9W.

The ligation reaction mixture was used to transform *Escherichia coli* DH10B and the transformed cells were plated on LB media that contained 20 μg/ml of tetracycline. Tetracycline-resistant tranformants that contained plasmids with the wild type loxP site correctly inserted into the PacI and FseI sites of pLDHTc139#7-9W were identified by restriction digest analysis, colony PCR using appropriate primers, and DNA sequence analysis of the relevant regions. The plasmid that was selected for further manipulation was named pLDHTc139#7-9WW, and a circle diagram of this construct is shown in FIG. 9B.

Construction of pLDHSp-9WW pLDHSp-9WW is identical to pLDHTc139#7-9WW, except that the tetracycline-resistance cassette in the latter construct was replaced with a DNA fragment that confers resistance to spectinomycin (i.e. a Spec$^r$-cassette). The latter was generated by PCR using plasmid pHP15578 (described in Cahoon et al, 2003) as a template and Primers 9 and 10 for PCR-amplification. pHP15578 contains the complete nucleotide sequence for the Spec$^r$ cassette, including its promoter, which is based on the published sequence of the Tranposon Tn7 aadA gene (GenBank accession number X03403) that codes for 3' (9)-O-nucleotidyltransferase.

Primer 9 (SEQ ID NO: 12):
ATAAAAgcggccgcAGCACAGGATGA

Primer 10 (SEQ ID NO: 13):
GGCGttaattaaGGCAGGTCAGCAAG

Figure 9C:
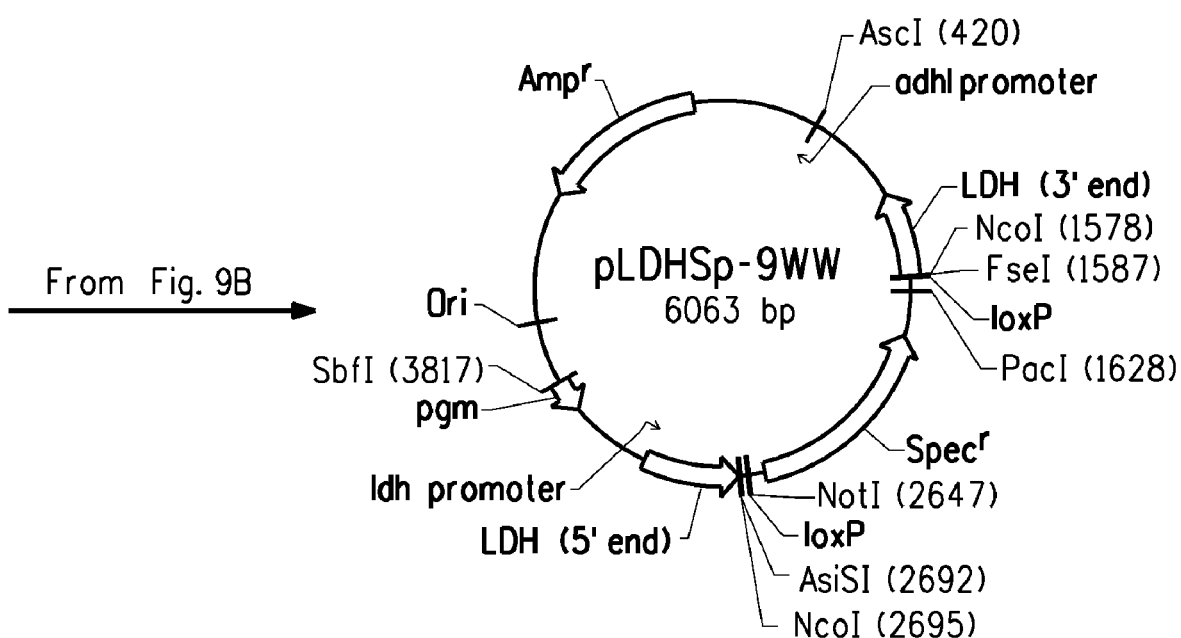

The underlined bases of Primer 9 (forward primer) hybridize just upstream from the promotor for the Spec$^r$ cassette (to nts 6-17 of GenBank accession number X03043), while the lower case letters correspond to a NotI site that was added to the 5' end of the primer. The underlined bases of Primer 10 (reverse primer) hybridize about 130 bases downstream from the stop codon for the Spec$^r$ cassette (to nts 1006-1019 of GenBank accession number X03043), while the lower case letters correspond to a PacI site that was added to the 5' end of the primer. The 1040 bp PCR-generated Spec$^r$ cassette was double-digested with NotI and PacI, and the resulting DNA fragment was purified by agarose gel electrophoresis. Plasmid pLDHTc139#7-9WW was also cut with the same two restriction enzymes to remove the Tc$^r$-cassette, and the resulting large vector fragment was purified by agarose gel electrophoresis. The PCR and vector fragments were then ligated together, and the transformation reaction mixture was introduced into *E. coli* DH10B using electroporation. Transformants were plated on LB media that contained spectinomycin (200 μg/ml) and grown at 37° C. Spectinomycin-resistant tranformants that contained plasmids with the correct size insert were identified by restriction digest analysis with NotI and PacI, and the plasmid that was selected for further manipulation was named pLDHSp-9WW; a circle diagram of this construct is shown in FIG. 9C.

In another project, pLDHSp-9WW was used to knockout the gene for D-lactate dehydrogenase in ZW1 using host-mediated, double-crossover, homologous recombination and growth on spectinomycin as the selection. The double-crossover event was targeted to the ldh gene by two DNA fragments that flank the Spec$^r$-cassette in the suicide construct. One of these fragments (referred to below as 5' ldh flanking DNA) is just upstream from the Spec$^r$-cassette and is located between the SbfI and AsiSI sites. The nucleotide sequence of this ~1100 bp DNA fragment is identical to the ZW1 chromosomal DNA that codes for the 3' end of the pgm gene and about the first half of the ldh open reading frame. The other DNA fragment (referred to below as the 3' ldh flanking DNA) is located at the opposite end the Spec$^r$-cassette between the FseI and AscI sites. The nucleotide sequence of the 3' ldh flanking DNA (which is also ~1100 bp) is identical to the chromosomal DNA that codes for the other half of the ldh gene and part of the 5' non-translated region of the adhI gene. A double-crossover event occurs when the 5' and 3' ldh flanking DNA fragments both interact with their chromosomal counterparts and undergo homologous recombination. This phenomenon, which is essentially irreversible and entirely mediated by the host's enzymatic machinery, inactivates the chromosomal ldh gene by inserting the Spec$^r$-cassette that is flanked by two wild type loxP sites in the middle of the open reading frame. Since the suicide construct cannot replicate in *Z. mobilis*, the only way to generate stable spectinomycin-resistant colonies with pLDHSp-9WW (apart from spontaneous drug resistant mutants that occur at a very low frequency) is a double-crossover event through homologous recombination.

Construction of pHimA

To generate a knockout construct for the himA gene, the ldh flanking DNA in pLDHSp-9WW was replaced with himA flanking DNA to target the selectable marker and double-crossover event to the chromosomal himA gene. Four DNA fragments were required for this manipulation as described below.

Fragment 1 was derived from pLDHSp-9WW (FIG. 9C) by cutting the plasmid with four different restriction enzymes: NotI, BsaI, SbfI and AscI. NotI cuts pLDHSp-9WW at nt 2647 and BsaI cuts the plasmid at nt 1816. After the plasmid DNA was completely digested with the four restriction enzymes, the 2666 bp SbfI-AscI DNA fragment was purified by electrophoresis using a 1% agarose gel and the Zymoclean Gel DNA Recovery Kit (catalog #D4001, Zymo Research). This fragment, named Fragment 1, contains an *E. coli* origin of replication that is not functional in *Z. mobilis* and a gene that confers ampicillin-resistance in *E. coli*.

Fragment 2 was also derived from pLDHSp-9WW. The plasmid was double-digested with FseI and AsiSI, and the resulting 1105 bp FseI-AsiSI DNA fragment was purified by electrophoresis using a 1% agarose gel and the Zymoclean Gel DNA Recovery Kit (catalog #D4001, Zymo Research) to clean up the fragment. This fragment, named Fragment 2, contains the Spec$^r$-cassette which is flanked by two wild type loxP sites, one at each end.

Fragment 3 contains 3' himA flanking DNA. The ~1.12 Kbp Fragment 3 was generated by PCR using Primers A and B. The template for PCR-amplification was genomic DNA that was isolated from ZW658 (ATCC #PTA-7858) using the Wizard Genomic DNA Purification Kit (catalog #A1125, Promega).

```
Primer A (SEQ ID NO: 14):
CTACTCATcctgcaggTTTAATGAATGAGCGGATGCTG

Primer B (SEQ ID NO: 15):
CATCTTACTgcgatcgcTGACTTTCCGTGCCAGCCAG
```

The underlined bases of Primer A (forward primer) hybridize to nucleotides 1137154-1137175 of the *Z. mobilis* genome (GenBank accession number AE008692) that are located in the middle of a coding region for a putative member of the glutathione S-transferase family of proteins (Seo et al., Nat. Biotechnol. 23 (1), 63-68 (2005)) that is downstream from the himA gene, while the lower case letters correspond to an SbfI site that was added to the 5' end of the primer. The underlined bases of Primer B (reverse primer) hybridize to nucleotides 1138276-1138257 of the *Z. mobilis* genome at the 3' end of the himA open reading frame, while the lower case letters correspond to an AsiSI site that was added to the 5' end of the primer. The chromosomal binding sites for Primers A and B and the PCR product that is generated (Fragment 3) are shown in FIG. 10A. The PCR product was digested with SbfI and AsiSI, and the resulting 1123 bp fragment was then purified by agarose gel electrophoresis as described above.

Fragment 4 contains 5' himA flanking DNA. The ~1.16 kb Fragment 4 was generated by PCR using Primers C and D. The template for PCR-amplification was genomic DNA that was isolated from ZW658 (ATCC #PTA-7858) using the Wizard Genomic DNA Purification Kit (catalog #A1125, Promega).

```
Primer C (SEQ ID NO: 16):
TCACTCATggccggccGGGATATCAGCTTGCATGCTC

Primer D (SEQ ID NO: 17):
CATCTTACTggcgcgccGATATGCTGCCTTCCGAAGTG
```

The underlined bases of Primer C (forward primer) hybridize to nucleotides 1138510-1138530 of the *Z. mobilis* genome at the 5' end the of himA open reading frame, while the lower case letters correspond to an FseI site that was added to the 5' end of the primer. The underlined bases of Primer D (reverse primer) hybridize to nucleotides 1139668-1139648 of the *Z. mobilis* genome upstream from the himA gene at the 3' end of a gene that presumably codes for a two-component response regulator (Seo et al., Nat. Biotechnol. 23 (1), 63-68 (2005)), while the lower case letters correspond to an AscI site that was added to the 5' end of the primer. The chromosomal binding sites for Primers C and D and the PCR product that is generated (Fragment 4) are shown in FIG. 10A. The PCR product was digested with FseI and AscI, and the resulting 1159 bp fragment was purified by electrophoresis using a 1% agarose gel.

The four DNA fragments described above were then subjected to a 4-way ligation reaction to assemble the himA knockout construct, pHimA shown in FIG. 10B. The molar ratio of Fragments 1-4 that was used for this reaction was approximately 1:1:1:1. An aliquot of the ligation reaction mixture was electroporated into *E. coli* DH10B and the transformed cells were plated on LB media that that contained ampicillin (100 μg/ml) and spectinomycin (100 μg/ml); the plates were incubated at 37° C. Ampicillin and spectinomycin double resistant tranformants that contained plasmids with the correct size inserts were initially identified by colony PCR using two different pairs of primers: Primer A/Primer B, and Primer C/Primer D. Subsequent confirmation of positive clones came from restriction digestion analysis of plasmid DNA with SbfI and AscI, and DNA sequence analysis of the pHimA plasmid DNA from the PCR positive clones.

To obtain non-methylated plasmid DNA needed for transformation of *Z. mobilis*, pHimA was introduced into *E. coli* SCS110 (dcm⁻, dam⁻), and the transformed cells were plated on LB media that contained ampicillin (100 μg/ml) and spectinomycin (100 μg/ml); growth was at 37° C. The chemically competent cells that were used for this manipulation were obtained from Stratagene (Cat. No. 200247) and the vendor's protocol was followed. It is important to note that the use of non-methylated plasmid DNA for transformation of *Z. mobilis* stains that are derived from ZM4 is critical for success, since methylated plasmid DNA that is isolated from wild type strains of *E. coli*, like DH10B, is readily destroyed by the host's restriction/modification system. In the last step, plasmid DNA was isolated from one of the SCS10 transformants using the QIAGEN Plasmid Maxi Kit (Cat. No. 12162), and the final concentration of DNA was ~2 μg/μl.

Example 6

Generation of the ZW801-4 himA Knockout Mutant

To inactivate the himA gene in ZW801-4, the non-methylated pHimA plasmid DNA (which does not replicate in *Z. mobilis*) was introduced into ZW801-4 using electroporation, essentially as described in U.S. Pat. No. 5,514,583. Briefly, the 50 μl transformation reactions contained ~$10^{10}$ cells/ml in 10% (v/v) glycerol and ~0.5 μg of non-methylated plasmid DNA that was isolated from *E. coli* SSC110 as described in Example 5. The control reaction was treated identically, but did not receive any plasmid DNA. The settings for the electroporator were 1.6 kv/cm, 200Ω, and 25 μF, and the gap width of the cuvette was 0.1 cm. After electroporation, the transformation reactions were diluted with 1.0 ml of MMG media (50 g/L glucose, 10 g/L yeast extract, 5 g/L of tryptone, 2.5 g/L of $(NH_4)_2SO_4$, 0.2 g/L $K_2HPO_4$, and 1 mM $MgSO_4$) and the cells were allowed to recover for ~3 hours at 30° C. The cells were then harvested by centrifugation at room temperature (13,000×g, 5 min) in sterile 1.5 ml microfuge tubes and the supernatant was carefully removed. Cell pellets were resupended in 200 □l of liquid MMG media, and 25-, 50- and 100 μl aliquots of the cell suspension were plated on MMG media that contained 1.5% agar and 200 □g/ml of spectinomycin. The plates were incubated in an anaerobic chamber at 30° C., and after 48-72 hrs there were at least 100 colonies on all of the experimental plates. In contrast, the control reaction only yielded one colony which was on the plate that received 100 μl of the cell suspension. Two of the spectinomycin-resistant colonies that resulted from transformation with the pHimA knockout construct were selected for further manipulation as described below.

Previous experiments in our laboratory with *Z. mobilis* and suicide constructs that are analogous to pHimA have revealed that the initial interaction between the chromosome and the plasmid DNA is a single-crossover event that takes place at one of the two flanking DNA sequences, and that single-crossover events eventually give rise to double-crossover events. Transition to the double-crossover event is normally very rapid and usually occurs after a few serial transfers in liquid or solid media that contains the selective agent for the suicide construct, in this case spectinomycin. To facilitate the double-crossover event for the present invention and rule out the possibility of obtaining a "mixed population" of single- and double-crossover events, the two primary transformants that were described above were patched onto an MMG plate that contained 200 µg/ml of spectinomycin. After a 30-hr incubation period at 33° C. under anaerobic conditions, single colonies were isolated from both patches by streaking the cells onto fresh agar plates that contained the same growth media. After a 30-hr incubation period at 33° C. under anaerobic conditions, one colony from each of the original primary transformants was patched onto a fresh MMG plate that contained spectinomycin (200 µg/ml), and these two strains were further characterized as described below.

Confirmation that the double-crossover event did occur and that each strain that was isolated consisted of a homogenous population of cells was obtained from colony PCR experiments using three different pairs of primers. The first pair of primers, GTTCTGCGCCTGTTATTCTG (SEQ ID NO: 18) and CTACCTCTGATAGTTGAGTCG (SEQ ID NO: 19), could only generate a PCR product of the correct size if the 5' himA flanking DNA in the suicide construct had undergone a single-crossover event with its chromosomal counterpart. Similarly, the second pair of primers, GATAT-TCCAGTGCTGATCGAC (SEQ ID NO: 20) and CTACGT-GAAAGGCGAGATCAC (SEQ ID NO: 21), could only generate a PCR product of the correct size if the 3' himA flanking DNA in the suicide construct had undergone a single-crossover event with its chromosomal counterpart. Finally, the third pair of primers, GATCAGGTAGGTGTGCTCTA (SEQ ID NO: 22) and GCATCAGAGAGCATACTGCT (SEQ ID NO: 23), could only generate a PCR product of the correct size if a double-crossover event had occurred at the correct locus. This pair of primers was also able to detect trace amounts of non-disrupted copies of the himA gene and/or single-crossover events if they were also present as contaminants. Since both of the himA knockout mutants that were examined yielded the expected results with three different sets of primers and appeared to be indistinguishable, only one of them was selected for further characterization. This strain is referred to below as "Z801-4::ΔhimA".

Example 7

Inactivation of the himA Gene is Solely Responsible for the AcR#3 Phenotype

A side-by-side comparison of ZW801-4 and ZW801-4:: ΔhimA in 100% MH using pH-controlled bioreactors is shown in FIG. 11. The seed cultures were grown at 30° C. in SM media to an $OD_{600}$ of ~4.4 and the bioreactors were started with a 10% inoculum. The final 150 ml cultures contained 100% MH plus 110 g/L glucose and 90 g/L xylose. The stirrer was set at 150 rpm, and pH and temperature were maintained at 5.8 and 33° C., respectively. At various times, aliquots were removed from the bioreactors for HPLC analysis of the fermentation broth using the procedure that is described in Example 2. Note that these are the exact same experimental conditions that were used for the experiments with AcR#3 and ZW801-4 that are shown in FIG. 8 and Table 2 (Example 4).

Figure 11A:
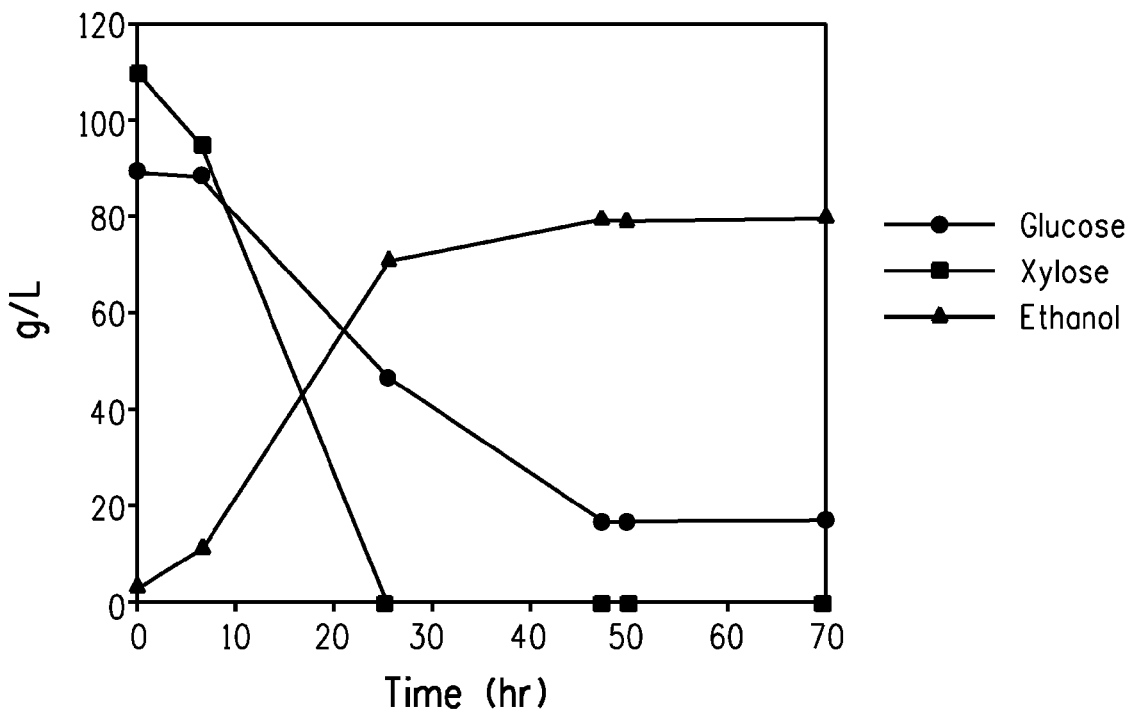
Figure 11B:
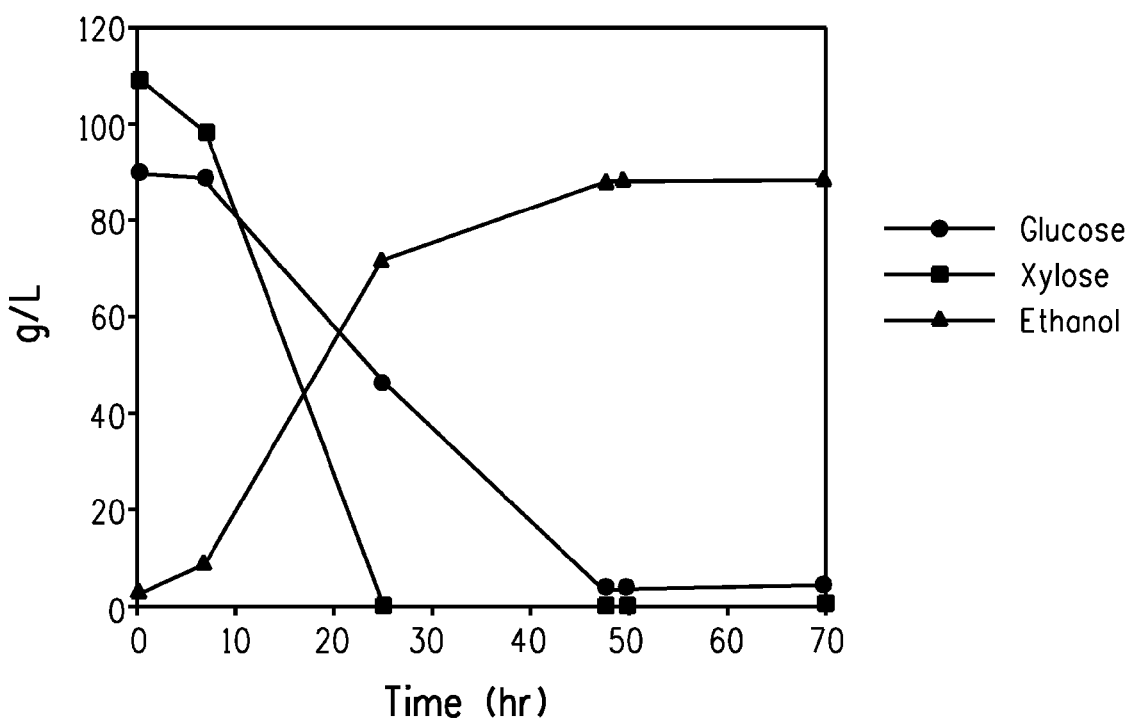

The results given in FIG. 11 show that ZW801-4::ΔhimA (FIG. 11B) performed much better than ZW801-4 (FIG. 11A) in 100% MH. By 48 hours it had used all of the glucose and xylose in the growth media and generated ~90 g/L of ethanol. In contrast, the parent strain, ZW801-4, did not use all of sugar and there was still ~17 g/L of residual xylose in the fermentation broth at the end of the experiment. The final ethanol titer for ZW801-4 was also significantly lower (81 g/L). Thus, inactivation of the himA gene resulted in about a 10% increase in ethanol production under process-relevant conditions, which is virtually identical to the results that were obtained with AcR#3 using the same experimental conditions. Although these results strongly suggested that AcR#3 and ZW801-4::ΔhimA are equivalent strains, it was important to test their performance in a side-by-side experiment. 100% MH was also used for this comparison, but the initial concentrations of glucose and xylose were both increased ~10%, since both strains were able to use all of the sugar in the earlier experiments.

Seed cultures were grown at 30° C. in SM media to an $OD_{600}$ of 4.5 and the bioreactors were started with a 10% inoculum. The final 150-ml cultures contained 100% MH plus 118 g/L glucose and 98 g/L xylose. The stirrer was set at 150 rpm, and pH and temperature were maintained at 5.8 and 33° C., respectively. At various times, aliquots were removed from the bioreactors for HPLC analysis of the fermentation broth using the procedure that is described in Example 2. The final values for glucose, xylose, acetate, ethanol and biomass production ($OD_{600}$) for both strains are shown in Table 3.

TABLE 3

End-point values for glucose, xylose, ethanol, and acetate in pH-controlled fermentors with ZW801-4::ΔhimA and AcR#3 strains grown in 100% Mock Hydrolysate with high sugar.

| Strain | Hours | $OD_{600}$ | Glucose | Xylose | Acetate | Ethanol |
|---|---|---|---|---|---|---|
| ZW801-4::ΔhimA | 0 | 0.48 | 118.2 | 98.4 | 10.0 | 3.9 |
| ZW801-4::ΔhimA | 70 | 6.3 | 0 | 14 | 10.5 | 90.7 |
| AcR#3 | 0 | 0.48 | 118.0 | 98.2 | 10.0 | 4.0 |
| AcR#3 | 70 | 6.2 | 0 | 14.1 | 10.4 | 90.6 |

The results from this experiment demonstrate that himA gene inactivation is solely responsible for the improved fermentation performance, since ZW801-4::ΔhimA and AcR#3 both behaved identically in the test system. These two strains were also indistinguishable when they were tested for acetate-resistance (FIG. 12) using the same conditions that were used for the experiment that is shown in FIG. 5. Clearly, the integrated Pgap promoter in the himA gene of AcR#3 and the prolonged mutant-enrichment process that this strain was subjected to had little or no effect on the desirable himA phenotype.

What is claimed is:

1. A process for producing ethanol from a mixed-sugars medium comprising xylose, comprising:
   (a) providing a recombinant *Zymomonas* strain capable of utilizing xylose to produce ethanol, said strain comprising at least one genetic modification which reduces expression of integration host factor alpha subunit protein (HimA); and
   (b) culturing the strain of (a) in a medium comprising xylose, whereby xylose is used by said strain as a carbon source for producing ethanol.

2. The process according to claim 1, wherein culturing is at a temperature range of from about 25° C. to about 40° C. in medium with pH in a range that is between about 4.5 and 7.5.

3. The process according to claim 2, wherein the temperature is between about 30° C. and 37° C.

4. The process according to claim 2, wherein the pH is between about 5.8 and 7.0.

5. The process according to claim 1, wherein the genetic modification is a modification of the himA gene selected from the group consisting of insertion, deletion, mutation, cosuppression, and antisense RNA expression.

6. The process according to claim 5, wherein the genetic modification makes the himA gene non-functional.

7. The process according to claim 6, wherein the genetic modification is an insertion introduced into the himA gene by homologous recombination.

8. The process according to claim 1, wherein the recombinant *Zymomonas* strain is ZW801-4:: ΔhimA or strain AcR#3 which are derived from strain ATCC PTA 7858.

9. The process according to claim 1, wherein the medium further comprises acetate and wherein the recombinant *Zymomonas* strain produces an increased amount of ethanol as compared to its parental *Zymomonas* strain with no genetic modification which reduces himA expression.

10. The process of claim 9, wherein said increased amount of ethanol produced is due to acetate resistance of the *Zymomonas* strain.

11. The process of claim 9, wherein the medium comprises at least about 120 g/L of mixed sugars comprising xylose, a sugar alcohol selected from the group consisting of sorbitol, mannitol, galactitol, ribitol, and a mixture thereof in a final concentration that is between about 2 mM and about 100 mM, and at least about 6 g/L acetate.

12. The process of claim 11, wherein the sugar alcohol is in a concentration that is between about 5 mM and about 20 mM.

* * * * *